US008410167B2

(12) United States Patent  (10) Patent No.: US 8,410,167 B2
Radzik et al. (45) Date of Patent: Apr. 2, 2013

(54) USE OF DRONEDARONE FOR THE PREPARATION OF A MEDICAMENT FOR USE IN THE PREVENTION OF CARDIOVASCULAR HOSPITALIZATION OR OF MORTALITY

(75) Inventors: Davide Radzik, Paris (FR); Martin Van Eickels, Berlin (DE); Nacéra Hamdani, Paris (FR); Christophe Gaudin, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 12/425,125

(22) Filed: Apr. 16, 2009

(65) Prior Publication Data

US 2010/0048694 A1 Feb. 25, 2010

Related U.S. Application Data

(60) Provisional application No. 61/045,995, filed on Apr. 18, 2008, provisional application No. 61/060,257, filed on Jun. 10, 2008, provisional application No. 61/151,611, filed on Feb. 11, 2009, provisional application No. 61/151,622, filed on Feb. 11, 2009, provisional application No. 61/159,956, filed on Mar. 13, 2009.

(30) Foreign Application Priority Data

| Apr. 17, 2008 | (FR) | 08 02127 |
| Jun. 10, 2008 | (FR) | 08 03208 |
| Feb. 11, 2009 | (EP) | 09290095 |
| Feb. 11, 2009 | (EP) | 09290098 |

(51) Int. Cl.
*A01N 43/08* (2006.01)
*A61K 31/34* (2006.01)

(52) U.S. Cl. .......... 514/461; 514/183; 514/469
(58) Field of Classification Search .......... 514/183
See application file for complete search history.

(56) References Cited

U.S. PATENT DOCUMENTS

| 4,988,513 | A | 1/1991 | Griffity |
| 5,223,510 | A | 6/1993 | Gubin et al. |
| 5,985,915 | A | 11/1999 | Frangin et al. |
| 6,218,414 | B1 | 4/2001 | Nisato |
| 6,297,287 | B1 | 10/2001 | Bergeron .......... 514/648 |
| 6,828,448 | B2 | 12/2004 | Fino et al. |
| 6,846,936 | B2 | 1/2005 | Biard |
| 6,939,865 | B2 | 9/2005 | Bourriague-Seve et al. |
| 6,951,844 | B2 | 10/2005 | Hangeland |
| 7,323,493 | B1 | 1/2008 | Abramovici et al. |
| 2001/0012900 | A1 | 8/2001 | Schouteeten et al. |
| 2002/0150622 | A1 | 10/2002 | Philbrook et al. |
| 2003/0073127 | A1 | 4/2003 | Ji et al. |
| 2003/0113330 | A1 | 6/2003 | Uhal |
| 2003/0229007 | A1 | 12/2003 | Levi et al. |
| 2004/0034220 | A1 | 2/2004 | Magerlein |
| 2005/0004194 | A1 | 1/2005 | Graves |
| 2005/0027331 | A1* | 2/2005 | Bardy .......... 607/60 |
| 2005/0070552 | A1 | 3/2005 | Fedida et al. |
| 2005/0182105 | A1 | 8/2005 | Nirschl et al. |
| 2005/0187267 | A1 | 8/2005 | Hamann et al. |
| 2005/0250783 | A1 | 11/2005 | Johnson et al. |
| 2006/0093673 | A1 | 5/2006 | Coury et al. |
| 2006/0135536 | A9 | 6/2006 | Fedida et al. |
| 2007/0243257 | A1 | 10/2007 | Bedos et al. |
| 2007/0248564 | A1 | 10/2007 | Wilson et al. |
| 2009/0076137 | A1 | 3/2009 | Czarnik |
| 2010/0016423 | A1 | 1/2010 | Claudel et al. |
| 2010/0320099 | A1 | 12/2010 | Scarazzini .......... 206/232 |
| 2011/0124724 | A1 | 5/2011 | Gaudin et al. |
| 2011/0136899 | A1 | 6/2011 | Radzik et al. |
| 2011/0166220 | A1 | 7/2011 | Gaudin et al. |
| 2011/0166221 | A1 | 7/2011 | Gaudin et al. |
| 2011/0230552 | A1 | 9/2011 | Gaudin et al. |
| 2012/0000806 | A1 | 1/2012 | Radzik et al. |
| 2012/0005128 | A1 | 1/2012 | Gaud et al. |

FOREIGN PATENT DOCUMENTS

| CN | 101152154 | 4/2008 |
| CN | 101153012 | 4/2008 |
| EP | 0338746 | 10/1989 |
| EP | 1782829 | 5/2007 |
| JP | 2004339218 A | 12/2004 |
| WO | WO 97/34597 | 9/1997 |
| WO | WO 98/40067 | 9/1998 |
| WO | WO 98/58643 | 12/1998 |
| WO | WO 99/64050 | 12/1999 |
| WO | WO 00/27380 | 5/2000 |
| WO | WO 02/15891 | 2/2002 |
| WO | WO 02/48132 A1 | 6/2002 |
| WO | WO 03/040120 A1 | 5/2003 |
| WO | WO 2005/018635 A2 | 3/2005 |
| WO | WO 2005/048979 A2 | 6/2005 |

(Continued)

OTHER PUBLICATIONS

U.S. Appl. No. 12/777,606, filed May 11, 2010, Scarazzini.
Agelaki et al, Comparative Antiarrhythmic Efficacy of Amiodarone and Dronedarone During Acute Myocardial Infarction in Rats, Eur J Pharmacol (2007) 564 pp. 150-157.
Aimond et al, Cellular and In Vivo Electrophysiological Effects of Dronedarone in Normal and Postmyocardial Infarcted Rats, JPET (2000) 292 pp. 415-424.
Altomare et al, Effects of dronedarone on Acetylcholine-activated current in rabbit SAN cells, Br J Pharmaco (2000) 130 pp. 1315-1320.
Anonymous, Dronedarone: dronedarone, SR33589, SR33589B, Drugs R D (2007) 8 (3) pp. 171-175.
Arlet et al, [Correspondence Related to Singh et al, NEJM (2007) 357 pp. 987-999] Dronedarone in Atrial Fibrillation, NEJM 2007 (357) 23 pp. 2403-2405.

(Continued)

Primary Examiner — Jeffrey S. Lundgren
Assistant Examiner — Meghan Finn
(74) Attorney, Agent, or Firm — Kelly L. Bender

(57) ABSTRACT

Methods of using dronedarone or a pharmaceutically acceptable salt thereof, for the preparation of a medicament for use in the prevention of cardiovascular hospitalization or of mortality, articles of manufacture and packages related thereto.

24 Claims, 5 Drawing Sheets

FOREIGN PATENT DOCUMENTS

| | | |
|---|---|---|
| WO | WO 2005/066149 A1 | 7/2005 |
| WO | WO 2005/105096 | 11/2005 |
| WO | WO 2006/032762 A2 | 3/2006 |
| WO | WO 2007/009462 A2 | 1/2007 |
| WO | WO 2007/039263 A2 | 4/2007 |
| WO | WO 2007/140989 A2 | 12/2007 |
| WO | WO 2008/044261 A1 | 4/2008 |
| WO | WO 2008/139057 A2 | 11/2008 |
| WO | WO 2008/141189 A1 | 11/2008 |
| WO | WO 2008/152217 A2 | 12/2008 |
| WO | WO 2009/044143 A2 | 4/2009 |
| WO | WO 2009/133310 A2 | 11/2009 |
| WO | WO 2009/133470 | 11/2009 |
| WO | WO 2009/150534 A1 | 12/2009 |
| WO | WO 2009/150535 A1 | 12/2009 |
| WO | WO 2010/015939 A1 | 2/2010 |
| WO | WO 2011/141872 | 11/2011 |

OTHER PUBLICATIONS

Aronow, Management of atrial fibrillation in the elderly, Minerva Med. (2009) 100 (1) pp. 3-24.
Bajpai et al, Treatment of atrial fibrillation, Br. Med. Bulletin (2008) 88 (1) pp. 75-94.
Barthelemy et al, Electrocardiographic Cardiovascular and Sympatholytic Action of Dronedarone, a New Antiarrhythmic Agent, in Conscious Dogs, J Mol Cell Cardiol (1998) 30 (6) pp. A3 (Abstract 2).
Bolderman et al, Determination of the class III antiarrhythmic drugs dronedarone and amiodarone, and their principal metabolites in plasma and myocardium by high-performance liquid chromatography and UV-detection, Journal of Chromatography B, 877 (2009) pp. 1727-1731.
Bollmann et al, Antiarrhythmnic Drugs in Patients with Implantable Cardioverter-Defibrillators, Am J Cardiovasc Drugs (2005) 5 (6) pp. 371-378.
Boriani et al, Pharmacological Cardioversion of Atrial Fibrillation. Current Management and Treatment Options, Drugs (2004) 64 (24) pp. 2741-2762.
Boyd et al, Dronedarone: Boon or bust?, Cardiology Review (2008) 25 (8) pp. 48-51.
Bril et al, Recent advances in arrhythmia therapy: treatment and prevention of atrial fibrillation, Curr Opinion Pharmacol (2002) 2 pp. 154-159.
Camm, Clinical differences between the newer antiarrhythmic agents, Europace Supplements (2000) 1 (Suppl. C) pp. C16-C22.
Camm, Safety considerations in the pharmacological management of atrial fibrillation, Int. J. Cardiol. (2008) 127 (3) pp. 299-306.
Camm et al, New antiarrhythmic drugs for atrial fibrillation: Focus on dronedarone and vernakalant, J Interv Card Electrophysiol (2008) 23 (1) pp. 7-14.
Castro et al, New Antiarrhythmic Drugs for the Treatment of Atrial Fibrillation, J Pacing and Clinical Electrophysiol (2002) 25 (2) pp. 249-259.
Celestino et al, Acute in vitro effects of dronedarone, an iodine-free derivative, and amiodarone, on the rabbi sinoatrial node automaticity: a comparative study, J Cardiovasc Pharmacol and Therapeutics (2007) 12 (3) pp. 248-257.
Chatelain et al, Interaction of the antiarrhythmic agents SR 33589 and amiodarone with the beta-adrenoceptor and adenylate cyclase in rat heart, Br J Pharmacol (1995) 116 pp. 1949-1956.
Coceani, Andromeda's Forgotten Glimmer, J Cardiovascular Electrophysiology (2006) 17 (12) p. E11.
Coleman et al, Dronedarone: An antiarrhythmic agent for the management of atrial fibrillation and atrial flutter, Formulary (2009) 44 (2) pp. 40-46.
Coletta et al, Clinical Trials update from Heart Rhythm 2008 and Heart Failure 2008: Athena, Urgent, INH study, Heart and CK-1827452, Eur J Heart Failure (2008) 10 pp. 917-920.
Coletta et al, Clinical trials update from the Heart Failure Society of America and the American Heart Association meetings in 2008: SADHART-CHF, Compare, Momentum, thyroid hormone analogue study, HF-Action, I-Preserve, B-interferon study, Bach, and Athena, Eur. J Heart Failure (2009) 11 (2) pp. 214-219.
Conway et al, New Horizons in Antiarrhythmic Therapy: Will Novel Agents Overcome Current Deficits?, Am. J Cardiol. (2008) 102 (Suppl) 6A pp. 12H-19H.
Cooper et al, Diuretics and risk of Arrhythmic Death in Patients With Left Ventricular Dysfunction, Circulation (1999) 100 pp. 1311-1315.
Cosnier et al, Amiodarone and Dronedarone Reduce Early Mortality in Post MI Rat, Fundam Clin Pharmacol (1999) 13 (Suppl. 1) pp. 73S (Abstract S35.7).
Crijns et al, Effects of Dronedarone on Clinical Outcomes in Patients with Atrial Fibrillation and Coronary Heart Disease: Insights from the ATHENA Study, Eur Heart J (2009) 30 (Suppl) p. 450 (Abstract 2779).
Dai, Two patterns of ion channelopathy in the myocardium: Perspectives for development of anti-arrhythmic agents, Curr Opin Investig Drugs (2005) 6 (3) pp. 289-297.
Dale et al, Dronedarone: an Amiodarone Analog for the Treatment of Atrial Fibrillation and Atrial Flutter, Annals of Pharmacotherapy (2007) 41 (4) pp. 599-605.
Damy et al, Pharmacokinetic and pharmacodynamic interactions between metoprolol and dronedarone in extensive and poor CYP2D6 metabolizers healthy subjects, Fundamental & Clinical Pharmacol (2004) 18 pp. 113-123.
Damy et al, Pharmacokinetic and pharmacodynamic interactions between metoprolol and dronedarone in healthy subjects, Fundamental & Clin Pharmacol (2003) 17 pp. 255 (Abstract P-170).
Davy et al, Dronedarone for the control of ventricular rate in permanent atrial fibrillation: The Efficacy and safety of Dronedarone for the control of ventricular rate during atrial fibrillation (ERATO) study, American Heart Journal (2008) 156 (3) pp. 527.e1-527.e9.
Davy et al, Effect of Dronedarone on Exercise in Patients with Permanent Atrial Fibrillation, Eur. Heart J (2006) 27 (Suppl. 1) pp. 885 Abstract P5154.
Davy et al, The efficacy and safety of dronedarone as a novel rate control agent for the treatment of atrial fibrillation, Eur Heart J (2005) 26 (Suppl. 1) pp. 505 Abstract P3042.
Djandjighian et al, Hemodynamic and Antiadrenergic Effects of Dronedarone and Amiodarone in Animals with a healed Myocardial Infarction, J Cardiovasc Pharmacol (2000) 36 (3) pp. 376-383.
Doggrell et al, Dronedarone: an amiodarone analogue, Expert Opin Investig Drugs (2004) 13 (4) pp. 415-426.
Ehrlich et al, Atrial-selective pharmacological therapy for atrial fibrillation: hype or hope?, Cur. Opin. Cardiol. (2009) 24 (1) pp. 50-55.
Ehrlich et al, Novel Approaches for Pharmacological Management of Atrial Fibrillation, Drugs, (2009) 69 (7) pp. 757-774.
Elizari et al, Pure Class III and Multiclass Antiarrhythmics: Electrophysiologic Remarks and Therapeutic Experiences (A326R0110). 9th Int'l Congress on Cardiovasc Pharmacotherapy (2000) pp. 113-121.
Finance et al, Effects of a New Amiodarone-Like Agent, SR 33589, in Comparison to Amiodarone, D,L-Sotalol, and Lignocaine, on Ischemia-Induced Ventricular Arrhythmias in Anesthetized Pigs, J Cardiovasc Pharmacol (1995) 26 (4) pp. 570-576.
Finance et al, Electrophysiological and Anti-Arrhythmic Actions of a New-Amiodarone-Like Agent, Dronedarone in Experimental Atrial Fibrillation, J Mol Cell Cardiol (1998) 30 (7) pp. A251 (Abstract 74).
Finance et al, Electrophysiological and Hemodynamic Effects of a New Amiodarone-Like Agent Following Acute and Chronic Oral Treatment in Anesthetized Dogs, J Mol Cell Cardiol (1998) 30 (7) pp. A251 (Abstract 75).
Gautier et al, Electrophysiologic Characterization of Dronedarone in Guinea Pig Ventricular Cells, J Cardiovasc Pharmacol (2003) 41 pp. 191-202.
Gautier et al, In Vivo and In Vitro Antiarrhythmic Effects of SSR149744C in Animal Models of Atrial Fibrillatior and Ventricular Arrhythmias, J Cardiovasc Pharmacol (2005) 45 (2) pp. 125-135.
Gautier et al, In Vivo and In Vitro Characterization of the Novel Antiarrhythmic Agent SSR149744C. Electrophysiological, Anti-Adrenergic, and Anti-Angiotensin II Effects, J Cardiovasc Pharmacol (2004) 44 (2) pp. 244-257.

Guillemare et al, Acute Effects of Dronedarone and Amiodarone on iK1, iKr and iKs in Guinea Pig Ventricular Myocytes, Fundam. Clin. Pharmacol. (1999) 13 p. 388 (Abstracts—French Pharmacological Society).

Guillemare et al, Inhibitory Effects of Dronedarone on Muscarinic K+ Current in Guinea Pig Atrial Cells, J Cardiovasc Pharmacol (2000) 36 (6) pp. 802-805.

Guiraudou et al, Involvement of Nitric Oxide in the Coronary Vasodilation Induced by Amiodarone and Dronedarone in the Isolated Guinea Pig Heart, Fundam Clin Pharmacol (1999) 13 (Suppl. 1) pp. 73S (Abstract S35.8).

Guiraudou et al, Involvement of nitric oxide in amiodarone- and dronedarone-induced coronary vasodilation in guinea pig heart, Eur J Pharmacol (2004) 496 pp. 119-127.

Guiraudou et al, Nitric oxide-dependent coronary relaxant effect of amiodarone and dronedarone in the isolated guinea pig heart, Archives of Pharmacol (1998) 358 pp. R299 (Abstract P18.16).

Gupta et al, Newer Antiarrhythmic Drugs, Indian Heart J (2001) 53 pp. 354-360.

Han et al, Benzofuran derivatives and the thyroid, Clinical Endocrinology (2009) 70 pp. 2-13.

Hodeige et al, SR 33589, a new amiodarone-like antiarrhythmic agent: anti-adrenoceptor activity in anaesthetized and conscious dogs, Eur J Pharmacol (1995) 279 pp. 25-32.

Hohnloser et al, Correction—Effect of dronedarone on cardiovascular events in atrial fibrillation, NEJM (2009) 360 (23) pp. 2487.

Hohnloser et al, Dronedarone Significantly Decreases the Combined Endpoint of Hospitalization and Death in Patients with Atrial Fibrillation, Circulation (1995) 112( 17) Supp II pp. II-327-II 328 (Abstract 1637).

Hohnloser et al, Effect of Dronedarone on Cardiovascular Events in Atrial Fibrillation, NEJM (2009) 360 (7) pp. 668-678.

Hohnloser et al, Effect of Dronedarone on Cardiovascular Outcomes: A Meta-analysis of Five Randomized Controlled Trials in 6157 Patients With Atrial Fibrillation/Flutter, J Am. Coll. Cardiol. (2009) 53 (10) Suppl. 1; e-Abstract 1020-54 pp. 1-7.

Hohnloser et al, Rationale and Design of ATHENA: A Placebo-Controlled Double-Blind, Parallel Arm Trial to Assess the Efficacy of Dronedarone 400 mg Bid for the Prevention of Cardiovascular Hospitalization or Death from any Cause in Patients with Atrial Fibrillation/Atrial Flutter, J Cardiovasc Electrophysiol (2008) 19 pp. 69-73.

Hynes et al, A review of the pharmacokinetics, electrophysiology and clinical efficacy of dronedarone, Future Cardiology (2005) 1 (2) pp. 135-144.

Indik et al, The Patient with Atrial Fibrillation, American J Med. (2009) 122 (5) pp. 415-418.

Iqbal et al, Recent developments in atrial fibrillation, Br Med J (2005) 330 pp. 238-243.

Ishii et al, Effects of dronedarone on the currents of Xenopus oocytes co-expressing HERG and KvLQt1/mink channels, J Mol Cell Cardiol (2005) 39 (6) pp. 1017-1018 (Abstract P-2-4).

Iwamoto et al, Na+/Ca2+ exchange inhibitors: a new class of calcium regulators, Cardiovas. & Hematolog. Disorders: Drug Targets (2007) 7 (3) pp. 188-198.

Kathofer et al, The Novel Antiarrhythmnic Drug Dronedarone: Comparison with Amiodarone, Cardiovascular Drug Reviews (2005) 23 (3) pp. 217-230.

Kayser, Dronedarone: In Quest of the Ideal Antiarrhythmic Drug, Prog. in Cardiovasc. Nursing (2007) 22 (4) pp. 221-224.

Khan, Oral class III antiarrhythmics: what is new?, Current Opin Cardiology (2004) 19 pp. 47-51.

Khoo et al, Acute Management of Atrial Fibrillation, Chest (2009) 135 (3) pp. 849-859.

Koeber et al, Increased Mortality after Dronedarone Therapy for Severe Heart Failure, NEJM (2008) 358 (25) pp. 2678-2687.

Kopceuch, ATHENA trial post hoc analysis shows dronedarone significantly reduced hospitalization incidence and duration, Cardiology Review, 26 (1) 2009 pp. 39.

Krishnamoorthy et al. Antiarrhythmic drugs for atrial fibrillation: focus on dronedarone, Expert Rev. Cardiovasc. Therapy (2009) 7 (5) pp. 473-481.

Lafuente et al, Antiarrhythmic Drugs for Maintaining Sinus Rhythm After Cardioversion of Atrial Fibrillation—A Systematic Review of Randomized Controlled Trials, Arch Intern Med (2006) 166 pp. 719-728.

Lagorce et al, Simultaneous Electrospray LC/MS/MS Assay Method of Dronedarone (SR33589) and its Debutyl Metabolite (SR35021) in Human Plasma, J Pharm Belg (1998) 53 (10) pp. 210 (Abstract).

Lalevee et al, Effects of Amiodarone and Dronedarone on Voltage-Dependent Sodium Current in Human Cardiomyocytes, J Cardiovasc Electrophysiol (2003) 14 pp. 885-890.

Laughlin et al, Dronedarone: A New Treatment for Atrial Fibrillation, J. Cardiovasc. Electrophysiol. (2008) 19 (11) pp. 1220-1226.

Le Grand, Dronedarone, IDrugs (2001) 4 (5) pp. 582-585.

Lee et al, IKr Channel Blockers: Novel Antiarrhythmic Agents, Curr Med Chem—Cardiovascular & Hematological Agents (2003) 1 pp. 203-223.

Lombardi et al, Pharmacological Treatment of Atrial Fibrillation: Mechanisms of Action and Efficacy of Class III Drugs, Current Med Chem (2006) 13 (14) pp. 1635-1653.

Manning et al, SR33589, a New Amiodarone-Like Agent: Effect on Ischemia- and Reperfusion-Induced Arrhythmias in Anesthetized Rats, J Cardiovas Pharmacol (1995) 26 (3) pp. 453-461.

Manning et al, SR 33589, a New Amiodarone-like Antiarrhythmic Agent: Electrophysiological Effects in Anesthetized Dogs, J Cardiovasc Pharmacol (1995) 25 (2) pp. 252-261.

Manoach et al, Hypokalema as a Simple Reproducible Model for Sustained Atrial Fibrillation, J Mol and Cell Cardiology (1998) 30(6) p. A4 (Abstract 8).

Mealy et al, Dronedarone Hydrochloride, Drugs Fut (2005) 30 (4) pp. 397-398.

Moro et al, In Vitro Effects of Acute Amiodarone and Dronedarone on Epicardial, Endocardial, and M Cells of the Canine Ventricle, J Cardiovasc Pharmacol. Therapeutics (2007) 12 (4) pp. 314-321.

Morrow et al, Drug Therapy for Atrial Fibrillation: What Will Its Role Be in the Era of Increasing Use of Catheter Ablation?, PACE, 32(1) 2009 pp. 108-118.

Morrow et al, New antiarrhythmic drugs for establishing sinus rhythm in atrial fibrillation: What are our therapies likely to be by 2010 and beyond?, Am Heart J (2007) 154 (5) pp. 824-829.

Muller et al, Clinical trial updates and hotline sessions presented at the European Society of Cardiology Congress 2008, Clin. Res. Cardiol. (2008) 97 (12) pp. 851-864.

Naccarelli et al, Atrial fibrillation and the expanding role of catheter ablation: Do antiarrhythmic drugs have a future?, J. Cardiovasc. Pharmacol. (2008) 52 (3) pp. 203-209.

Naccarelli et al, New antiarrhythmic treatment of atrial fibrillation, Expert Rev. of Cardiovasc. Ther. (2007) 5 (4) pp. 707-714.

Naccarelli et al, Old and New Antiarrhythmic Drugs for Converting and Maintaining Sinus Rhythm in Atrial Fibrillation: Comparative Efficacy and Results of Trials, Am J Cardiol (2003) 91 (suppl) pp. 15D-26D.

Nattel et al, New Approaches to Atrial Fibrillation Management. A Critical Review of a Rapidly Evolving Field, Drugs (2002) 62 (16) pp. 2377-2397.

Norota et al, Inhibitory effects of dronedarone and amiodarone on HERG+KvLQT1/minK currents, J Pharmacol Sci (2006) 100 (Suppl. 1) pp. 221P Abstract P2M-08.

Ocasio et al, Clinical prospects for new thyroid hormone analogues, Curr Opinion Endocrinol and Diabetes (2005) 12 pp. 363-370.

Pantos et al, Blockage of thyroid hormone receptor alpha 1 suppresses food intake and potentiates thyroxine effect on body weight reduction, Eur Heart J (2005) 26 (Suppl. 1) pp. 608 Abstract P3612.

Pantos et al, Dronedarone Administration Prevents Body Weight Gain and Increases Tolerance of the Heart to Ischemnic Stress: A Possible Involvement of thyroid Hormone Receptor alpha1, Thyroid (2005) 15 (1) pp. 16-23.

Pantos et al, Effects of dronedarone and amiodarone on plasma thyroid hormones and on the basal and postischemic performance of the isolated rat heart, Eur J Pharmacol (2002) 444 pp. 191-196.

Pantos et al, Pharmacological inhibition of TRalpha1 receptor potentiates the thyroxine effect on body weight reduction in rats: potential therapeutic implications in controlling body weight, Diabetes, Obesity & Metabolism (2007) 9 (1) pp. 136-138.

Pantos et al, Thyroid Hormone Receptor A1: A New Pharmacological Target for Cardioprotection and Body Weight Control, Epitheorese Klin. Farmakol. Farmakokinet. (2008) 26 (1) pp. 36-37.

Pecini et al, New antiarrhythmic agents for atrial fibrillation and atrial flutter, Expert Opin Emerging Drugs (2005) 10 (2) pp. 311-322.

Pedersen et al, The immediate future for the medical treatment of atrial fibrillation, Expert Opin Emerging Drugs (2002) 7 (2) pp. 259-268.

Pitt et al, Chronic amiodarone-induced inhibition of the Na+-K+ pump in rabbit cardiac myocytes is thyroid-dependent: comparison with dronedarone, Cardiovascular Res (2003) 57 pp. 101-108.

Quaglino et al, Effects of metabolites and analogs of amiodarone on alveolar macrophages: structure-activity relationship, Am J Physiol Lung Cell Mol Physiol (2004) 287 pp. L438-L447.

Ridley et al, High affinity HERG K+ channel blockade by the antiarrhythmic agent dronedarone: resistance to mutations of the S6 residues Y652 and F656, Biochem Biophys Research Comm (2004) 325 pp. 883-891.

Riera et al, Relationship among amiodarone, new class III antiarrhythmics, miscellaneous agents and acquirec long QT syndrome, Cardiology Journal (2008) 15 (3) pp. 209-219.

Rocchetti et al, Cellular Electrophysiological Study of Dronedarone, a New Amiodarone-Like Agent, in Guinea Pig Sinoatrial Node, Archives of Pharmacology (1998) 358 (Suppl.2) pp. R617 (Abstract P 36.13).

Rochetaing et al, Beneficial Effects of Amiodarone and Dronedarone (SR 33589b), when Applied During Low-Flow Ischemia, on Arrhythmia and Functional Parameters Assessed during Reperfusion in Isolated Rat Hearts, J Cardiovasc Pharmacol (2001) 38 (4) pp. 500-511.

Sablayrolles et al, Drug evaluation: Dronedarone, a novel non-iodinated anti-arrhythmmic agent, Current Opinion in Investigational Drugs (2006) 7 (9) pp. 842-849.

Schmitt et al, New Antiarrhythmic Drugs for the Treatment of Atrial Fibrillation, Herz (2008) 33 (8) pp. 562-567.

Serre et al, Lack of proarrhythmic effect of dronedarone and amiodarone in a rabbit model of torsades de pointes. Comparison with dofetilide, Fundamental & Clinical Pharmacol (2001) 15 (Suppl. 1) p. 45 (Abstract 7P202).

Shi et al, Long-term Effects of Amiodarone and its Non-iodinated Analogue, Dronedarone, on the Transcription of Cardiac Sarcoplasmic Reticulum Ca2+—ATPase Gene, Environmental Med (2003) 47 pp. 39-41.

Shimizu et al, Effects of Dronedarone on HERG and KCNQ1/KCNE1 Channels, Environmental Med (2003) 47 pp. 48-50.

Sicouri et al, Dronedarone and Amiodarone Reduce Transmural Dispersion of Repolarization in the Canine Heart, Fundam Clin Pharmacol (1999) 13 (Suppl. 1) pp. 72S (Abstract S35.5).

Singh, Trials of New Antiarrhythmic Drugs for Maintenance of Sinus Rhythmn in Patients with Atrial Fibrillation, J Intervent Cardiac Electrophysiol (2004) 10 pp. 71-76.

Singh et al, Amiodarone as Paradigm for Developing New Drugs for Atrial Fibrillation, J Cardiovasc Pharmacol (2008) 52 (4) pp. 300-305.

Singh et al, Amiodarone: A Multifaceted Antiarrhythmic Drug, Current Cardiology Reports (2006) 8 pp. 349-355.

Singh et al, Dronedarone for Maintenance of Sinus Rhythm in Atrial Fibrillation or Flutter, NEJM (2007) 357 (10) pp. 987-999.

Singh et al, Dronedarone: rhythm and rate control in management of atrial fibrillation. Focus on Symptomatic Arrhythmia, Eur. Heart J (2006) 27 (Suppl. 1) p. 33 Abstract P440.

Singh et al, Mechanisms of Action of Antiarrhythmic Drugs Relative to the Origin and Perpetuation of Cardiac Arrhythmias, J Cardiovasc Pharmacol Therapeut (2001) 6 (1) pp. 69-87.

Singh et al, Mechanisms of Antiarrhythmic Actions in the Maintenance of Sinus Rhythm in Patients with Atrial Fibrillation: Clinical and Experimental Correlations, Atrial Fibrillation: New Therapeutic Concepts, Papp et al., Eds., (2003) pp. 41-55.

Stoykov et al, Effect of amiodarone and dronedarone administration in rats on thyroid hormone-dependent gene expression in different cardiac components, Eur J of Endocrinology (2007) 156 (6) pp. 695-702.

Sun et al, Acute Effects of Dronedarone on Potassium Currents in Isolated Rabbit Ventricular Myocytes. Comparison With Amiodarone, J Am Coll Cardiol (2000) 2 (Suppl. A) p. 98A (Abstract 1030-99).

Sun et al, Acute Effects of Dronedarone on the Potassium Currents in Human Atrial Cells, J Am Coll Cardiol (2002) 39 (5) Suppl. A p. 105A (Abstract 1136-115).

Sun et al, Chronic and Acute Effects of Dronedarone on the Action Potential of Rabbit Atrial Muscle Preparations: Camparison With Amiodarone, J Cardiovascul Pharmacol (2002) 39 (5) pp. 677-684.

Sun et al, Dronedarone Acutely Inhibits L-Type Calcium Currents and Alters the Channel Kinetics in Rabbit Ventricular Myocytes, J Am Coll Cardiol (2001) 37 (Suppl. A) p. 114A (Abstract 1202-112).

Sun et al, Electrophysiological Effects of Dronedarone (SR33589), a Noniodinated Benzofuran Derivative, in the Rabbit Heart. Comparison With Amiodarone, Circulation (1999) 100 pp. 2276-2281.

Tafreshi et al, A Review of the Investigational Antiarrhythmic Agent Dronedarone, J of Cardiovasc. Pharmacol. and Therapeutics (2007) 12 (1) pp. 15-26.

Tamargo et al, Pharmacology of cardiac potassium channels, Cardiovascular Res. (2004) 62 pp. 9-33.

Tedelind et al, Amiodarone Inhibits Thyroidal Iodide Transport in Vitro by a Cyclic Adenosine 5'-Monophosphate- and Iodine-Independent Mechanism, Endocrinology (2006) 147 (6) pp. 2936-2943.

Tejani et al, [Correspondence related to Hohnloser et al, NEJM (2009) 360 pp. 668-678] Dronedarone in Atrial Fibrillation, NEJM (2009) 360 (23) pp. 2479-2481.

Thomas et al, Acute effects of dronedarone on both components of the cardiac delayed rectifier K+ current, HERG and KvLQT1/minK potassium channels, Br J Pharmacol (2003) 140 pp. 996-1002.

Touboul et al, Dronedarone for prevention of atrial fibrillation: A dose-ranging study, Eur Heart J (2003) 24 pp. 1481-1487.

Tschuppert et al, Effect of Dronedarone on Renal Function in Healthy Subjects, Br. J. Clinical Pharmacol. (2007) 64 (6) pp. 785-791.

Van Beeren et al, Dronedrarone Acts as a Selective Inhibitor of 3,5,3'-Triiodothyronine Binding to Thyroid Hormone Receptor-alpha1: In Vitro and in Vivo Evidence, Endocrinology (2003) 144 (2) pp. 552-558.

Van Opstal et al, Chronic Amiodarone Evokes Number Torsade de Pointes Arrhythmias Despite QT Lengthening in an Animal Model of Acquired Long-QT Syndrome, Circulation (2001) 104 pp. 2722-2727.

Vanoli et al, Dronedarone, A New Amiodarone-Like Compound, Prevents Ventricular Fibrillation in Conscious Dogs with a Healed Myocardial Infarction, Fundam Clin Pharmacol (1999) 13 (Suppl. 1) pp. 73S (Abstract S35.61.

Varro et al, Comparison of the Cellular Electrophysiological Effects of Amiodarone and Dronedarone in Canine Ventricular Muscle and Purkinje Fibers, Fundam Clin Pharmacol (1999) 13 (Suppl. 1) pp. 72S (Abstract S35.4).

Varro et al, Electrophysiological effects of dronedarone (SR33589), a noniodinated amiodarone derivative in the canine heart: comparison with amiodarone, Br J Pharmacol (2001) 133 pp. 625-634.

Varro et al, Pharmacology of Potassium Channel Blockers, Atrial Fibrillation: New Therapeutic Concepts, Papp et al., Eds., (2003) pp. 27-39.

Varro et al, The cellular cardiac electrophysiological effects of dronedarone a new amiodarone like antiarrhythmic agent, Cardiovasc Drugs and Therapy (2000) 14 (2) p. 206 (Abstract 200).

Varro et al, Theoretical Possibilities for the Development of Novel Antiarrhythmic Drugs, Current Med Chem (2004) 11 pp. 1-11.

Verduyn et al, Evaluation of the Acute Electrophysiologic Effects of Intravenous Dronedarone, an Amiodarone-Like Agent, with Special Emphasis on Ventricular Repolarization and Acquired Torsade de Pointes Arrhythmias, J Cardiovasc Pharmacol (1999) 33 (2) pp. 212-222.

Vos, Preclinical Evaluation of Antiarrhythmic Drugs: New Drugs Should be Safe to be Successful, J Cardiovasc Electrophysiol (2001) 12 (9) pp. 1034-1036.

Vos et al, Anti-Arrhythmic Drugs and Torsade de Pointes Arrhythmias: An Experimental Approach, Fundam Clin Pharmacol (1999) 13 (Suppl. 1) p. 71S (Abstract S35.2).

Wadhani et al, Dose-Dependent Effects of Oral Dronedarone on the Circadian Variation of RR and QT Intervals in Healthy Subjects: Implications for Antiarrhythmic Actions, J Cardiovasc Pharmacol and Therapeutics (2006) 11 (3) pp. 184-190.

Walker, Antiarrhythmic drug research, Br J of Pharmacology (2006) 147 (Suppl. 1) pp. S222-S231.

Watanabe et al, Acute inhibitory effect of dronedarone, a noniodinated benzofuran analogue of amiodarone, on Na+/Ca2+ exchange current in guinea pig cardiac ventricular myocytes, Naunyn-Schmiedeberg's Arch. Pharmacol (2008) 377 pp. 371-376.

Watanabe et al, Effect of dronedarone on NA+/Ca2+ exchange current: comparison with amiodarone, J Pharmacol Sci (2003) 91 (Suppl. 1) pp. 141P (Abstract 1P214).

Watanabe et al, Inhibitory effect of dronedarone on Na+/Ca2+ exchange current in guinea pig cardiac myocytes: comparison with amiodarone, J Mol Cell Cardiology (2003) 35 p. A31 (Abstract P-25; 20th Annual Meeting, Inter'l Soc for Heart Research).

Watanabe et al, Topics on the NA+/Ca2+ Exchanger: Pharmacological Characterization of Na+/Ca2+ Exchanger Inhibitors, J Pharmacol Sci (2006) 102 pp. 7-16.

Wegener et al, Dronedarone: An Emerging Agent with Rhythm- and Rate-controlling Effects, J Cardiovasc. Electrophysiol. (2006) 17 (Supp 2) pp. S17-S20.

White, Is dronedarone effective for the prevention of recurrent atrial fibrillation?, Nature Clin Prac Cardiovasc Med (2008) 5 (3) pp. 136-137.

Wijffels et al, Atrial Fibrillation Begets Atrial Fibrillation—A Study in Awake Chronically Instrumented Goats, Circulation (1995) 92 pp. 1954-1968.

Wyse, Pharmacologic approaches to rhythm versus rate control in atrial fibrillation—where are we now?, Int. J Cardiology (2006) 110 pp. 301-312.

Zareba, Dronedarone: A New Antiarrhythmic Agent, Drugs of Today (2006) 42 (2) pp. 75-86.

Zimetbaum, Dronedarone for Atrial Fibrillation—An Odyssey, NEJM (2009) 360 (18) pp. 1811-1813.

Zunkler, Human ether-a-go-go-related (HERG) gene and ATP-sensitive potassium channels as targets for adverse drug effects, Pharmacology & Therapeutics (2006) 112 (1) pp. 12-37.

ClinicalTrials.gov/archive—View of NCT00174785 on Sep. 14, 2005—ATHENA: A Trial with Dronedarone to Prevent Hospitalization or Death oin Patients with Atrial Fibrillation, [on-line] This page was last modified on Jun. 9, 2010.

International Search Report, PCT/IB2009/005587.

Preliminary Search Report, FR 0803208.

Anderson et al. (1981) "Oral Flecainide Acetate for the Treatment of Ventricular Arrhythmias," *N. Engl. J. Med.* 305:473-77.

Echt et al. (1991) "Mortality and Morbidity in Patients Receiving Encainide, Flecainide, or Placebo," *N. Engl. J. Med.* 324:781-88.

Doyle et al. (2009) "Benefits and Risks of Long-term Amiodarone Therapy for Persistent Atrial Fibrillation: A Meta-analysis" *Mayo Clin. Proc.* 84:234-42.

Wyse et al. (2004) "Alternative endpoints for mortality in studies of patients with atrial fibrillation: The AFFIRM study experience," *Heart Rhythm* 1:531-37.

Wyse et al. (2002) "A Comparison of Rate Control and Rhythm Control in Patients with Atrial Fibrillation," *N. Engl. J. Med.* 347:1825-33.

Stein (2005) "Dronedarone Provides Multiple Benefits in Atrial Fibrillation: Presented at AHA," Doctor's Guide Personal Edition, 2 pages.

"El tratamiento con dronedarona en pacientes con arritmia cardiaca reduce el número de hospitalizaciones según un estudio," (2005), 2 pages.

Andreev, et al., A rise in plasma creatinine that is not a sign of renal failure: which drugs can be responsible?, J. of internal Medicine, 1999 (246) pp. 247-252.

Baker, New Drugs Approved by the FDA New Dosage Forms and Indications Agents Pending FDA Approval Significant Labeling Changes, Hospital Pharmacey, vol. 41, No. 11, (2008), pp. 1086-1089.

Bertuso, Do Patients With Cardiac Arrest and Hypoalemia Require Antiarrhythmic-Drug Therapy?, American Heart Association Monograph, American Heart Association. (1984), vol. 107, pp. II-443—abstract.

Butte, et al., [Amiodaron for treatment of perioperative cardiac arrythmia, a broad spectrum antiarrythmetic agent?]. Amiodaron zur Therapie perioperativer kardialer Rhythmusstorungen : Ein Breitspektrumantiamhythmikum?, Der Anaesthesist, (Dec. 2008) vol. 57, No. 12, pp. 1183-1192.

Camm, et al., Heart Failure and Sudden Death: Future Use of Antiarrhythmic Drugs and Devices, European Heart Journal Supplements, (2003), vol. 5, (Supplement I), pp. 1108-1115.

Connolly, Effect of Dronedarone on Stroke and Other Cardiovascular Outcomes, (Sep. 2008) Retrieved from the Internet: URL:http://resources.escardio.org/Webcast/ESC-2008/4482, [Retrieved on Feb. 6, 2012].

Connolly, S., et al., Comparison of B-Blockers, Amiodarone Plus B-Blockers, or Sotalol for Prevention of Shocks From Implantable Cardioverter Defibrillators: The Optic Study: a Randomized Trial, JAMA The Journal of the American Medical Association, American Medical Association, vol. 295, No. 2, pp. 165-171.

Cosnier-Pucheu, et al., Effects of Serum Albumin on Amiodarone and Dronodarone Tissue Distribution and Cardiac Function in the Perfused Rat Heart, Arch. Pharmacol., (vol. 358, No. 1, Suppl. 2, (1998), p. 36.29.

Davy, et al., [Atrial antiarrhythmics: Perspectives]. Antiarythmiques a l'etage atrial: Perspectives Archives des Maladies du Coeur et des Vaisseaux, (Dec. 2006) vol. 99, No. SPEC. ISS. 5, pp. 23-29.

Dickstein, et al., Effects of losartan and captopril on mortality and morbidity in high-risk patients after acute myocardial infarction: the OPTIMAAL randomised trial, Lancet, 2002 (360) pp. 752-760.

Ecker-Schlipf, [Antiarrhythmics: Dronedarone—An alternative to amiodarone, but with less side effects?]. Antiarrhythmika: Dronedaron: Nubenwirkungsarmere alternative zu amiodaron?, Krankenhauspharmazie, (Nov. 2008) vol. 29, No. 11, pp. 513-515. Refs: 1.

Fessler, [Heart arrhythmia: Dronedarone as alternative to amiodarone in atrial fibrilation]. Herzrhythmusstorungen: Dronedaron: Alternative zu amiodaron bei vorhofflimmern. Deutsche Apotheker Zeitung, (Oct. 14, 2004) vol. 144, No. 42, pp. 41-43.

Fikret, et al. [Stabilization of sinus rhythm with dronedarone in patients with atrial fibrillation? Comment: The safety of dronedarone has not been definitively clarified]. Rhythmusstabilisierung mit dronedaron bei patienten mit vorhoitlimmern? Kommentar: Sicherheit von dronedaron noch nicht abschliessend geklart. Deutsche Medizinische Wochenschrift, (Nov. 9, 2007) vol. 132, No. 45, pp. 2363.

Frazosi, et al., Indications for ACE Inhibitors in the Early Treatment of Acute. Myocardial Infarction: Systematic Overview of Individual Data From 100 000 Patients in Randomized Trials, Circulation, 1998 (97) pp. 2202-2212.

Gage, et al., Selecting Patients With Atrial Fibrillation for Anticoagulation: Stroke Risk Stratification in Patients Taking Aspirin, Circulation. (2004), vol. 110, pp. 2287-2292.

Gautier, et al., Electrophysiological Characterization of Dronedarone (SR 33589), A New Amiodarone-Like Agent, in Cardiac Ventricular Myocytes, Eur. Heart J., (18. Abstr. Suppl., 269, 1997).

Gensthaler, et al, [Dronedarone—A new hope for patients with atrial fibrillation]. Dronedaron—Neue hoffnung bei vorhofflimmern, Pharmazeutische Zeitung, (Sep. 11, 2008) vol. 153, No. 37, pp. 34.

Groch, New Antiarhythmic Agent Shows Promise for A-Fib, http://www.medpagetoday.com/Cardiology/Arrhythmias/6598, pp. 1-3, (2007).

Groenefeld, et al., Dronedarone as relapse prophylaxis after cardioversion of atrial fibrillation: results of a randomised, placebo-controlled, dose-finding study. Z.Kardiol. (92, Suppl, 1, V601, 2003).

Guillemare, et al., Effects of Dronedarone on Calcium Handling in Cardiac Ventricular Myocytes, Eur. Heart J. Supplements vol. 1, (20, Abstract Suppl., 329, 1999, Abstract 1749).

Hodeige, et al., SR 33589—Effect on Atrial Fibriliation in Dogs: Comparison With Amiodarone, European Section Meeting, International Societ for Heart Research, 15th, Copenhagen, Jun. 8-11, 1994, Meeting Date 1994, 681-684.
Huang et al., Pharmacological cardioversion of atrial fibrillation, Zhongguo Xinyao Yu Linchuang Zazhi (2007), 26(8), 631-635.
Klein, [Dronedarone—A new therapeutic option for controlling atrial rhythm and ventricular frequency]. Dronsdaron—Eine nsue therapeutische option zur kontrolle von vorhofrhythmus und kammerfrequenz, Deutsche Medizinische Wochenschrift, (Sep. 8, 2006) vol. 131, No. 34-35 Suppl., pp. S113-S117.
Le Grand, Dronedarone Sanofi-Synthelabo, Current Opinion in Cardiovascular, Pulmonary & Renal Investigational Drugs, (2000), vol. 2, No, 1, pp. 36-39.
Lewalter, et al., Pharmacotherapy of supraventriculair arrhythmias., Internist (47, No. 1, 80-1,83-8, 2006.
Liu, et el., Dronedarone: A novel antiarrhythmic drug for the treatment of atrial fibrillation. Pharmaceutical Care and Research, (Dec. 2008) vol. 8, No. 6, pp. 417-420.
Pfeffer, et al., Effect of Captopril on Mortality and Morbidity in Patients with Left Ventricular Dysfunction After Myocardial Infarction, NEJM, 1992 (327) 10 pp. 669-677.
Phillips, et al., Clinical Disorders of Potassium Homeostasis: Hyperkalemia and Hypokalemia, Veterinary Clinics of North America: Small Animal Practice, vol. 28, No. 3, pp. 545-564, (1998).
Pitt, et al., Eplerenone, a Selective Aldosterone Blocker, in Patients with Left Ventricular Dysfunction after Myocardial Infarction, NEJM, 2003 (348) 14 pp. 1309-1321.
Pitt, et al., The Effect of Spironolactone on Morbidity on Mortality in Patients with Severe Heart Failure, NEJM, 1909 (341) 11 pp. 709-717.
Pollak, et al., Creatinine elevation in patients receiving amiodarone correlates with serum amiodarone concentration, Br J Clin Pharmac, 1993 (36) pp. 125-127.
Pollak, et al., Changes in Serum Urea and Creatinine During Long-Term Therapy with Amiodarone, Clinical Pharmacology and Therapeutics, vol. 75, No. 2, P5, PI-9, (2004).
Preobrazhenskii, How Did Athena Win Andromeda? Results of the Athena., Kardiologiia, (2009), vol. 49, No. 4, pp. 63-64.
Preobrazhenski, et al., Efficacy of dronedarone in cardiac failure due to severe left ventricular systolic dysfunction. Results of the Andromeda., Kardiologiia, (2008) vol. 48, No. 12, pp. 67.
Preorazhenskii, et al., Efficacy of dronedarone for maintenance of sinus rhythm in atrial fibrillation or flutter. Results of the EURIDIS and ADONIS., Kardiologiia, (2008) vol. 48, No. 7, pp. 58-59.
Prystowsky, et al., Case Studies with the Experts: Management Decisions in Atrail Fibrillation, J. Cardiovasc Electrophysiol., vol. 19, pp. 1-12, Suppl. 1, (2008).
Purerfellner, et al., Athena-Studie: Vorlaufige Ergebnisse und Deren Mogliche Auswirkungen auf die Antiarrhythmische Pharmakotherapie bei Vorhofflimmern. Journal Fuer Kardiologie, Krause Und Pachemegg, vol. 15, No. 7-8, (2003), pp. 253-254.
Roy, et al., Rhythm Control Versus Rate Control for Atrial Fibrillation and Heart Failure, The New England Journal of Medicine, vol. 358, No. 25, (2008) pp. 2667-2677.
Sarma, et al., Dose-Dependent Effects of Dronedarone on the Circadian Patterns of RR and QT Intervals in Healthy Subjects, Circulation, (102, No. 18, Suppl. 802, 2000, Abstract 3874).
Schauerte, et al., Drug therapy of atrial fibrillation., Med.Welt (56, No. 9, 370-5, 2005).
Schwender, [Dronedarone establishes and maintains control of sinus rhythm]. Controle du rythme en cas de fibrillation auriculaire. La dronedarone retablit et maintient le rythme sinusal. Revue medicale suisse, (Aug. 23, 2006) vol. 2, No. 76, pp. 1902-1903.
Seelig, et al., Nephrotoxicity Associated with Concomittant ACE Inhibitor Medical NSAID Therapy, Southern Medical Journal, vol. 83, No. 10, pp. 1144-1148, (1990).
Stiles, S., et al., FDA Advisory Recommends Dronedarone Approval for Atrial Fibrillation, (2009). URL:www.theheart.org/article/949121.do [Retrieved on Jul. 21, 2010].
Swedberg, et al., Effects of the Early Administration of Enalapril on Mortality in Patients with Acute Myocardial Infarction, NEJM, 1992 (327) 10 pp. 678-684.
Touboul, et al., [New anti-arrhythmics—Hope or disappointment?], Nouveaux anti-arythmiques—Espoir ou deception?, Archives des Maladies du Coeur et des Vaisseaux, (Nov. 2004) vol. 97, No. 11, pp. 1048-1053.
Vanoli, et al., Dronedarone, A New Amiodarone-Like Compound, Prevents Ventricular Fibrillation in Conscious Dogs With a Healed Myocardial Infarction, Circulation, (98, No. 17, Suppl. 1817, 1998, Abstract 4286).
Vos, et al., Absence of Torsade de Pointes Arrhythmias Despite QT-Lengthening After Oral Amiodarone Treatment in an Animal Model of Acquired Long QT, Eur. Heart J., (22, Abstract Suppl. 449, 2001, Abstract P2366).
Wood, Euridis and Adonis: Dronedarone Bests Placebo for Sinus Rhyth, but Amiodarone Comparison Data Needed, http://www.theheart.org/article/809207.doc, pp. 1-2, (2007).
Wu, et al., Medication of heart failure and atrial fibrillation, Zhongguo Shiyong Neike Zazhi (2008), 28(6), 429-431.
Yusuf, et al., Effects of an Angiotensin-Converting—Enzyme Inhibitor, Ramipril, on Cardiovascular Events in High-Risk Patients, NEJM, 2000 (342) 3. pp. 145-153.
Dronedarone, Merck Index, 14th. Merck & Co. (2007)—No. 0003449, Characterizing Dronedarone as an Anti-arrhythmic, pp. 1-2.
Multaq (Dronedarone) Briefing Document, Advisory Committee Meeting of the Cardiovascular and Renal Drugs Division of the US Food and Drug Administration, Mar. 18, 2009.
Risk Evaluation and Mitigation Strategy (REMS), (2009), http://www.fda.gov/downloads/Drugs/Drugsafety/PostmarketDrugSafetyInformationforPatentsandProvides/UCM187494.pdf.
Sanofi-Aventis: Prescribing Information, (2009), http://products.sanofi-aventis.us/Multaq/Multaq.pdf.
Summary Minutes of the Cardiovascular and Renal Drugs Advisory Committee Mar. 19 2009, Retrieved from the Internet: URL:http://www.fda.gov/downloads/AdvisoryCommittees/commiteesMeetingMaterials/Drugs/CardiovascularandRenalDrugsAdvisoryCommittee/UCM151691.pfd [retrieved on Jul. 21, 2010].
Deutsche Apotheker Zietung, (May 5, 2008) vol. 148, No. 23, pp. 47-48, [Dronedarone for antiarrhythmic therapy]. Dronedaron zur anti-arrhythmischen therapie.
Benjamin, et al., Independent Risk Factor for Atrial Fibrillation in a Population-Based Cohort, JAMA, (1994), vol. 271, No. 11, pp. 840-844.
Khan, et al., Pharmacological Cardioversion of Recent Onset Atrial Fibrillation, European Heart Journal, (2004), vol. 25, pp. 1274-1276.
Morady, et el., The Treatment of Atrial Fibrillation, University of Michigan Electrophysiology Service, (2009), pp. 1-12.
U.S. Appl. No. 12/431,830—Final Office Action dated Jun. 7, 2011.
U.S. Appl. No. 12/431,830—Non-Final Office Action dated Oct. 29, 2010.
U.S. Appl. No. 12/951,471—Non-Final Office Action dated Jun. 22, 2012.
U.S. Appl. No. 12/962,102—Non-Final Office Action dated Jun. 18, 2012.
U.S. Appl. No. 12/962,115—Non-Final Office Action dated Jun. 21, 2012.
U.S. Appl. No. 12/431,830—Non-Final Office Action dated Jun. 20, 2012.
U.S. Appl. No. 13/211,673—Non-Final Office Action dated Jun. 13, 2012.
U.S. Appl. No. 12/903,374—Non-Final Office Action dated Nov. 23, 2012.

* cited by examiner

Months

Months

USE OF DRONEDARONE FOR THE PREPARATION OF A MEDICAMENT FOR USE IN THE PREVENTION OF CARDIOVASCULAR HOSPITALIZATION OR OF MORTALITY

The present invention relates to the use of dronedarone or pharmaceutically acceptable salts thereof, for the preparation of a medicament for use in the prevention of cardiovascular hospitalization and/or of mortality.

2-n-Butyl-3-[4-(3-di-n-butylaminopropoxy)benzoyl]-5-methylsulphonamidobenzofuran, or dronedarone, and pharmaceutically acceptable salts thereof are described in European Patent EP 0 471 609 B1.

Dronedarone blocks potassium, sodium and calcium channels and also has anti-adrenergic properties.

Dronedarone is an anti-arrhythmic that is effective in maintaining sinus rhythm in patients presenting with atrial fibrillation or atrial flutter.

The applicant has clinically proven that dronedarone significantly reduces cardiovascular hospitalizations and/or mortality in patients having a history of atrial fibrillation or of atrial flutter, by virtue of its ability to modulate the blood potassium level in a safe and effective way.

In fact, the use of benzofuran derivatives to reduce post-infarction mortality in patients having a reduced left ventricular function after myocardial infarction, without any rhythm disorder requiring an anti-arrhythmic treatment, is known from Patent Applications WO 98/40067 and WO 97/34597.

However, these applications neither disclose nor suggest the use of dronedarone to reduce cardiovascular hospitalizations and mortality in patients having a history of atrial fibrillation or atrial flutter, in particular by virtue of its ability to modulate the potassium level in the blood.

Potassium is the principal intracellular ion and plays an essential role in physiology.

Specifically, this ion is the principal osmotically active intracellular ion and plays an important role in the regulation of intracellular volume.

A constant and stable potassium concentration is essential for the function of enzyme systems and also for good growth and cell division.

Potassium contributes to establishing the resting potential of the cell membrane and, consequently, changes in potassium concentration, in particular in the extracellular compartment, have effects on cell excitability in the nervous, muscle and cardiac system.

A decrease in potassium concentration is known to increase cardiac hyperexcitability at the ventricular level, which can result in serious, potentially deadly, rhythm disorders.

The deleterious role of a decrease in potassium concentration has been documented in disparate clinical situations.

For example, in patients suffering from heart failure, the decrease in potassium concentration can lead to deadly rhythm disorders; diuretics having a "potassium sparing" effect have demonstrated a beneficial effect in this population.

The rapid decrease in potassium concentrations occurring following the abrupt arrest of intense physical exercise could also be responsible for certain sudden deaths.

A possible contribution of the decrease in potassium concentrations has been mentioned in the sudden death of patients treated with antipsychotics and also in acute alcohol withdrawal syndromes.

Eating habits with a reduced potassium intake may lead to sudden death in predisposed individuals, even without any structural cardiac pathology.

The risk of fatal cardiac hyperexcitability is particularly great in patients who receive an anti-arrhythmic treatment which prolongs the duration of cell repolarization, such as sotalol (Sotalex®). These agents may in fact induce a torsade de pointe, which is a severe and potentially deadly ventricular tachycardia. Torsades de pointes are facilitated by the decrease in potassium concentration.

Finally, it has been shown that the decrease in potassium concentration induces atrial fibrillations (Manoach M., J. Mol. Cell. Cardiol., 1998, 30(6): A4[8]).

Another clinical situation where the risk of potentially fatal cardiac rhythm disorders is high is represented by patients treated with diuretics, these medicaments, which are widely prescribed in many indications, the most common being arterial hypertension, but also heart failure, renal insufficiency, nephrotic syndrome, cirrhosis and glaucoma, expose the patient to the risk of a decrease in potassium concentration except for "potassium sparing" diuretics.

A complication of the decrease in potassium concentration subsequent to treatment with diuretics may be sudden death, in particular in patients who present an impairment of the contractile function of the heart or left ventricular dysfunction or after a myocardial infarction.

Regulation of the potassium concentration could therefore play an important beneficial role, in particular in the population of patients who require an anti-arrhythmic treatment (for atrial fibrillation) and who possibly have other risk factors.

Now, no anti-arrhythmic, to date, in therapy, has shown effects with regard to the regulation of the potassium level in the blood.

Atrial fibrillation (AF) affects about 2.3 million people in North America and 4.5 million people in the European Union and is emerging as a growing public health concern because of the aging of the population.

AF is a condition in which the upper chambers of the heart beat in an uncoordinated and disorganized fashion, resulting in a very irregular and fast rhythm (i.e., an irregularly, irregular heartbeat). When blood is not completely pumped out of the heart's chambers, it can pool and clot. If a blood clot forms in the atria, exits the heart and blocks an artery in the brain, a stroke results. Consequently, about 15 percent of strokes result from AF.

AF is increasingly frequent with advancing age and is often caused by age-related changes in the heart, physical or psychological stress, agents that stimulate the heart, such as caffeine, or as a result of cardiovascular disease. The number is expected to double in the next 20 years. Without appropriate management, AF can lead to serious complications, such as stroke and congestive heart failure.

It is known that atrial fibrillation itself can cause changes in the electrical parameters of the heart known as electrical remodelling and in the structure of the cardiac chambers known as structural remodelling which tend to decrease the chances of the patient to get back into normal sinus rhythm. This vicious circle whereby "atrial fibrillation begets atrial fibrillation" has been well documented since the 1990s (Wijffels M C, Kirchhof C J, Dorland R, Allessie M A. Atrial fibrillation begets atrial fibrillation. A study in awake chronically instrumented goats. Circulation. 1995 Oct. 1; 92(7): 1954-68). It explains why when patients have been in atrial fibrillation for a long time they develop permanent atrial fibrillation with little or no chance to recover from this arrhythmia which becomes chronic.

A subject of the present invention is therefore the use of dronedarone or a pharmaceutically acceptable salt thereof, for the preparation of a medicament, wherein said medicament is taken, for use in the prevention of cardiovascular hospitalizations and/or of mortality.

Said prevention of cardiovascular hospitalizations and/or of mortality is provided to patients having a history of atrial fibrillation or atrial flutter.

A subject of the present invention is therefore the use of dronedarone or a pharmaceutically acceptable salt thereof, for the preparation of a medicament for use in the prevention of cardiovascular hospitalizations and/or of mortality notably in patients having a history of atrial fibrillation or atrial flutter.

A subject of the present invention is specifically the use of dronedarone or a pharmaceutically acceptable salt thereof, for the preparation of a medicament for use in the prevention of cardiovascular hospitalizations and/or of mortality notably in patients having a history of atrial fibrillation or atrial flutter through regulation of the potassium level in the blood.

Mention may in particular be made of cardiovascular mortality, and more particularly sudden death, also called sudden cardiac death or sudden death from cardiovascular causes.

A subject of the present invention is also the use of dronedarone or a pharmaceutically acceptable salt thereof, for the preparation of a medicament, taken twice a day with a meal, for use in the prevention of mortality and/or of cardiovascular hospitalizations notably in patients having a history of atrial fibrillation or atrial flutter More specifically, a subject of the present invention is the use of dronedarone or a pharmaceutically acceptable salt thereof, for the preparation of a medicament for use in the prevention of approximately 24% of cardiovascular hospitalizations and/or of mortality in patients having a history of atrial fibrillation or atrial flutter, by regulating the potassium level in the blood.

A subject of the present invention is also the use of dronedarone or a pharmaceutically acceptable salt thereof, for the preparation of a medicament for use in the prevention of approximately 25% of cardiovascular hospitalizations and/or of cardiovascular mortality in patients having a history of atrial fibrillation or atrial flutter, by regulating the potassium level in the blood.

A subject of the present invention is also the use of dronedarone or a pharmaceutically acceptable salt thereof, for the preparation of a medicament for use in the prevention of approximately 26% of cardiovascular hospitalizations and/or of sudden death in patients having a history of atrial fibrillation or atrial flutter, by regulating the potassium level in the blood.

A subject of the present invention is also the use of dronedarone or a pharmaceutically acceptable salt thereof, in patients having a history of atrial fibrillation or atrial flutter, for the preparation of a medicament for use in the prevention:
  of cardiovascular hospitalizations, and more particularly of approximately 25% of cardiovascular hospitalizations, and/or
  of mortality, particularly of approximately 15% of mortality, and more particularly of approximately 16% of mortality, and/or
  of cardiovascular mortality, and more particularly of approximately 30% of cardiovascular mortality, and/or
  of arrhythmic death, and more particularly of approximately 45% of arrhythmic death.
  of sudden death, and more particularly of approximately 59% of sudden death and/or Another subject of the instant invention is the use of dronedarone or one of its pharmaceutically acceptable salts for the preparation of a medicament for use in the prevention of cardiovascular hospitalization and/or of mortality notably in patients with permanent atrial fibrillation or atrial flutter.

More precisely, the invention relates to the use of dronedarone or one of its pharmaceutically acceptable salts for the preparation of a medicament for the prevention of about 33% of cardiovascular hospitalization and/or of mortality notably in patients with permanent atrial fibrillation or atrial flutter.

Another subject of the instant invention is the use of dronedarone or one of its pharmaceutically acceptable salts for the preparation of a medicament for use in the prevention of cardiovascular hospitalization and/or of mortality notably in patients with a history of atrial fibrillation or atrial flutter and with structural heart disease particularly structural heart disease in a stable hemodynamic condition.

More precisely, the invention relates to the use of dronedarone or one of its pharmaceutically acceptable salts for the preparation of a medicament for the prevention of about 24% of cardiovascular hospitalization and/or of mortality notably in patients with a history of atrial fibrillation or atrial flutter and with structural heart disease in a stable hemodynamic condition.

More precisely, the invention relates to the use of dronedarone or one of its pharmaceutically acceptable salts for the preparation of a medicament for use in the prevention of about 24% of cardiovascular hospitalization notably in patients with a history of atrial fibrillation or atrial flutter and with structural heart disease in a stable hemodynamic condition.

More precisely, the invention relates to the use of dronedarone or one of its pharmaceutically acceptable salts for the preparation of a medicament for use in the prevention of about 24% of mortality notably in patients with a history of atrial fibrillation or atrial flutter and with structural heart disease in a stable hemodynamic condition.

More precisely, the invention relates to the use of dronedarone or one of its pharmaceutically acceptable salts for the preparation of a medicament for use in the prevention of about 33% of cardiovascular mortality notably in patients with a history of atrial fibrillation or atrial flutter and with structural heart disease in a stable hemodynamic condition.

Said structural heart disease may be coronary heart disease and/or Ischemic dilated cardiomyopathy and/or non-ischemic dilated cardiomyopathy and/or rheumatic valvular heart disease and/or non-rheumatic valvular heart disease and/or hypertrophic cardiomyopathy and/or LVEF<45% and/or history of congestive heart failure wherein congestive heart failure may be defined for example as NYHA class III or by a reduced left ventricular ejection fraction below 0.35.

NYHA means New York Heart Association.

Mention may be made that congestive heart failure is a sub-group of heart failure. Thus, the subject of the instant invention is also the use of dronedarone or one of its pharmaceutically acceptable salts for the preparation of a medicament for use in the prevention of cardiovascular hospitalization and/or of mortality notably in patients with a history of atrial fibrillation or atrial flutter and with congestive heart failure in a stable hemodynamic condition.

In an embodiment, the subject of the instant invention is the use of dronedarone or one of its pharmaceutically acceptable salts for the preparation of a medicament for use in the prevention of cardiovascular hospitalization and/or of mortality notably in patients with a history of atrial fibrillation or atrial flutter and with congestive heart failure defined as NYHA class III in a stable hemodynamic condition.

In an embodiment, the subject of the instant invention is the use of dronedarone or one of its pharmaceutically acceptable salts for the preparation of a medicament for use in the prevention of cardiovascular hospitalization and/or of mortality notably in patients with a history of atrial fibrillation or atrial flutter and with congestive heart failure defined by a reduced left ventricular ejection fraction below 0.35 in a stable hemodynamic condition.

More precisely, the invention relates to the use of dronedarone or one of its pharmaceutically acceptable salts for the preparation of a medicament for use in the prevention of about 44% of cardiovascular hospitalization and/or of mortality notably in patients with a history of atrial fibrillation or atrial flutter and with congestive heart failure defined as NYHA class III in a stable hemodynamic condition.

More precisely, the invention relates to the use of dronedarone or one of its pharmaceutically acceptable salts for the preparation of a medicament for use in the prevention of about 32% of cardiovascular hospitalization and/or of mortality notably in patients with a history of atrial fibrillation or atrial flutter and with congestive heart failure defined by a reduced left ventricular ejection fraction below 0.35 in a stable hemodynamic condition.

In an embodiment, the invention relates to the use of dronedarone or one of its pharmaceutically acceptable salts for the preparation of a medicament for use in the prevention of mortality notably in patients with a history of atrial fibrillation or atrial flutter and with congestive heart failure in a stable hemodynamic condition.

More precisely, the invention relates to the use of dronedarone or one of its pharmaceutically acceptable salts for the preparation of a medicament for use in the prevention of about 34% of mortality notably in patients with a history of atrial fibrillation or atrial flutter and with congestive heart failure defined as NYHA class III in a stable hemodynamic condition.

More precisely, the invention relates to the use of dronedarone or one of its pharmaceutically acceptable salts for the preparation of a medicament for use in the prevention of about 45% of death in patients with a history of atrial fibrillation or atrial flutter and with congestive heart failure defined with a left ventricular ejection fraction below 0.35 in a stable hemodynamic condition.

In an embodiment, the invention relates to the use of dronedarone or one of its pharmaceutically acceptable salts for the preparation of a medicament for use in the prevention of the worsening or development of congestive heart failure notably in patients with a history of atrial fibrillation or atrial flutter.

More precisely, the invention relates to the use of dronedarone or one of its pharmaceutically acceptable salts for the preparation of a medicament for use in the prevention of about 22% of the worsening or development of congestive heart failure NYHA class IV in patients with a history of atrial fibrillation or atrial flutter.

Patients with heart failure in a stable hemodynamic condition may be defined as patients without heart failure in an unstable hemodynamic condition.

In general, patients with heart failure in an unstable hemodynamic condition may be defined as patients with a severe heart failure and said severe heart failure may be defined by any of the following:
  worsening symptoms of heart failure at rest or with minimal exertion or,
  history of, or current symptoms of congestive heart failure at rest or,
  symptoms of heart failure with minimal exertion within the last month, i.e. the month prior to start of treatment or,
  hospitalization for heart failure within the last month, i.e. the month prior to start of treatment,
  NYHA Class IV,
  NYHA Class III within the last month,
  recent decompensation as indicated by the need for hospitalization or intravenous therapy, for example intravenous inotropic or diuretic therapy,
  recent decompensation requiring hospitalization or intravenous therapy for the treatment of heart failure.

Therefore, the invention also relates to the use of dronedarone or pharmaceutically acceptable salts thereof for preparing a medicament for use in the treatment of atrial fibrillation or flutter or for use in the prevention of mortality and/or of cardiovascular hospitalization in patients without severe heart failure.

A subject of the instant invention also relates to dronedarone or one of its pharmaceutically acceptable salts for the treatment of atrial fibrillation or flutter in patients without severe heart failure, a therapeutic amount of dronedarone or pharmaceutically acceptable salt thereof being administered.

In one embodiment, the invention relates to dronedarone or one of its pharmaceutically acceptable salts for the treatment of atrial fibrillation or flutter in patients without severe heart failure, wherein severe heart failure is indicated by one or more of the following:
  a) a history of, or current symptoms of congestive heart failure;
  b) symptoms of heart failure with minimal exertion within the last month;
  c) hospitalization of the patient for heart failure within the last month;
  d) hospitalization of the patient for NYHA Class IV heart failure;
  e) hospitalization of the patient for NYHA Class III heart failure within the last month,
  f) hospitalization of the patient for heart failure with recent decompensation as indicated by the need for hospitalization or intravenous therapy; and
  g) hospitalization of the patient for heart failure with recent decompensation requiring hospitalization or intravenous therapy for the treatment of heart failure.

In another embodiment, the invention relates to dronedarone or one of its pharmaceutically acceptable salts for the treatment of atrial fibrillation or flutter in patients without severe heart failure, wherein severe heart failure is indicated by hospitalization of the patient for NYHA Class IV heart failure.

In another embodiment, the invention relates to dronedarone or one of its pharmaceutically acceptable salts for the treatment of atrial fibrillation or flutter in patients without severe heart failure, wherein severe heart failure is indicated by hospitalization of the patient for NYHA Class III heart failure within the last month, i.e., one month prior to administration of dronedarone or one of its pharmaceutically acceptable salts.

Another subject of the invention is performed by providing dronedarone or pharmaceutically acceptable salts thereof, wherein said dronedarone or pharmaceutically acceptable salts thereof is provided along with information indicating that dronedarone or pharmaceutically acceptable salts thereof is indicated in patients with a recent history of or current atrial fibrillation or flutter and without severe heart failure.

In one embodiment, the information indicates that the atrial fibrillation or flutter is non-permanent. In another embodiment, the information indicates that the atrial fibrillation or flutter is associated with at least one risk factor. In another embodiment, the information indicates that severe heart failure is indicated by symptoms of heart failure with minimal exertion within the last month. In another embodiment, the information indicates that severe heart failure is indicated by hospitalization for heart failure within the last month. In another embodiment, the information indicates that severe heart failure is indicated by a history of, or current symptoms of congestive heart failure at rest. In another embodiment, the information indicates that severe heart failure is indicated by hospitalization of the patient for NYHA Class IV heart failure. In another embodiment, the information indicates that severe heart failure is indicated by hospitalization of the patient for NYHA Class III heart failure within the last month. In another embodiment, the information indicates that severe heart failure is indicated by hospitalization of the patient for heart failure with recent decompensation as indicated by the need for hospitalization or intravenous therapy.

In an embodiment of the invention, the information comprises printed matter that advises that dronedarone or pharmaceutically acceptable salts thereof is indicated in patients with either a recent history of or current atrial fibrillation or flutter with associated risk factors and without severe heart failure. In another embodiment, the printed material is a label.

The term "providing" includes selling, distributing, shipping, offering for sell, importing etc.

Mention may be made that "dronedarone for the treatment of" may be understood as "use of dronedarone for the preparation of a medicament for use in the treatment of".

The treatment of atrial fibrillation or flutter with dronedarone or a pharmaceutically acceptable salt thereof may be contra-indicated for patients with severe heart failure as indicated by any of the following:
- worsening symptoms of heart failure at rest or with minimal exertion or,
- history of, or current symptoms of congestive heart failure at rest or,
- symptoms of heart failure with minimal exertion within the last month, i.e. the month prior to start of treatment or,
- hospitalization for heart failure within the last month, i.e. the month prior to start of treatment,
- NYHA Class IV,
- NYHA Class III within the last month,
- recent decompensation as indicated by the need for hospitalization or intravenous therapy, for example intravenous inotropic or diuretic therapy,
- recent decompensation requiring hospitalization or intravenous therapy for the treatment of heart failure.

The invention also relates to the use of dronedarone or pharmaceutically acceptable salts thereof for preparing a medicament for use in the treatment of atrial fibrillation or flutter or for use in the prevention of mortality and/or of cardiovascular hospitalizations wherein said medicament is contra-indicated for patients with severe heart failure as indicated by any of the following:
- worsening symptoms of heart failure at rest or with minimal exertion or,
- history of, or current symptoms of congestive heart failure at rest or,
- symptoms of heart failure with minimal exertion within the last month, i.e. the month prior to start of treatment or,
- hospitalization for heart failure within the last month, i.e. the month prior to start of treatment,
- NYHA Class IV,
- NYHA Class III within the last month,
- recent decompensation as indicated by the need for hospitalization or intravenous therapy, for example intravenous inotropic or diuretic therapy,
- recent decompensation requiring hospitalization or intravenous therapy for the treatment of heart failure.

The invention also relates to a method of promoting the use of dronedarone or pharmaceutically acceptable salts thereof, the method comprising the step of conveying to a recipient at least one message selected from the group consisting of:

(a) dronedarone or pharmaceutically acceptable salts thereof should be prescribed to a patient who has not been diagnosed with severe heart failure;

(b) dronedarone or pharmaceutically acceptable salts thereof is contraindicated in patients with a history of or current symptoms of congestive heart failure;

(c) dronedarone or pharmaceutically acceptable salts thereof is contraindicated in patients with severe heart failure;

(d) dronedarone or pharmaceutically acceptable salts thereof is contraindicated in patients with symptoms of heart failure with minimal exertion within the last month; and (e) dronedarone or pharmaceutically acceptable salts thereof is contraindicated in patients who were hospitalized for heart failure within the last month, (f) dronedarone or pharmaceutically acceptable salts thereof is contraindicated in patients who were hospitalized for NYHA Class IV heart failure, (g) dronedarone or pharmaceutically acceptable salts thereof is contraindicated in patients who were hospitalized for NYHA Class III heart failure within the last month, (h) dronedarone or pharmaceutically acceptable salts thereof is contraindicated in patients who were hospitalized for heart failure with recent decompensation as indicated by the need for hospitalization or intravenous therapy, for example intravenous inotropic or diuretic therapy, (i) dronedarone or pharmaceutically acceptable salts thereof is contraindicated in patients who were hospitalized for heart failure with recent decompensation requiring hospitalization or intravenous therapy for the treatment of heart failure.

The invention also relates to a method of promoting the use of dronedarone or a pharmaceutically acceptable salt thereof, the method comprising the step of conveying to a recipient at least one message selected from the group consisting of a) a primary endpoint of a study of dronedarone, or a pharmaceutically acceptable salt thereof, was the time to first hospitalization for cardiovascular reasons or death from any cause;

b) a secondary endpoint of a study of dronedarone, or pharmaceutically acceptable salt thereof, was death from any cause;

c) a secondary endpoint of a study of dronedarone, or a pharmaceutically acceptable salt thereof, was time to death from any cause;

d) a secondary endpoint of a study of dronedarone, or a pharmaceutically acceptable salt thereof, was time to cardiovascular death;

e) a secondary endpoint of a study of dronedarone, or a pharmaceutically acceptable salt thereof, was time to first hospitalization for cardiovascular reasons;

f) a secondary endpoint of a study of dronedarone, or a pharmaceutically acceptable salt thereof, was time to first hospitalization for atrial fibrillation and other supraventricular rhythm disorders;

g) a secondary endpoint of a study of dronedarone, or a pharmaceutically acceptable salt thereof, was time to first hospitalization for worsening heart failure;

h) a secondary endpoint of a study of dronedarone, or a pharmaceutically acceptable salt thereof, was time to first hospitalization for myocardial infarction;

i) a secondary endpoint of a study of dronedarone, or a pharmaceutically acceptable salt thereof, was time to first hospitalization for myocardial infarction;

j) a secondary endpoint of a study of dronedarone, or a pharmaceutically acceptable salt thereof, was time to first hospitalization for transient ischemic event or cerebral stroke;

k) a secondary endpoint of a study of dronedarone, or a pharmaceutically acceptable salt thereof, was time to sudden death;

l) dronedarone, or a pharmaceutically acceptable salt thereof, reduced the combined endpoint of cardiovascular hospitalization or death from any cause by about 24 percent;

m) dronedarone, or a pharmaceutically acceptable salt thereof, reduced the combined endpoint of cardiovascular hospitalization or death from any cause by 24.2 percent;

n) dronedarone, or a pharmaceutically acceptable salt thereof, reduced the combined endpoint of cardiovascular hospitalization or death from any cause by 24.2 percent, driven by a reduction in cardiovascular hospitalization; and o) 70 percent of patients enrolled in a study of dronedarone, or a pharmaceutically acceptable salt thereof, had no heart failure.

In one embodiment, the message is provided in a label or package insert.

The invention also concerns an article of manufacture comprising
a) a packaging material;
b) dronedarone or pharmaceutically acceptable salts thereof, and
c) a label or package insert contained within the packaging material indicating that dronedarone or pharmaceutically acceptable salts thereof is contraindicated in patients with severe heart failure.

In some embodiments, the packaging material indicates that dronedarone or pharmaceutically acceptable salts thereof is contraindicated in patients with severe heart failure indicated by one or more of the following:

a) a history of, or current symptoms of congestive heart failure;
b) symptoms of heart failure with minimal exertion within the last month;
c) hospitalization of the patient for heart failure within the last month;
d) hospitalization of the patient for NYHA Class IV heart failure;
e) hospitalization of the patient for NYHA Class III heart failure within the last month,
f) hospitalization of the patient for heart failure with recent decompensation as indicated by the need for hospitalization or intravenous therapy; and
g) hospitalization of the patient for heart failure with recent decompensation requiring hospitalization or intravenous therapy for the treatment of heart failure.

The invention also relates to a package comprising dronedarone or pharmaceutically acceptable salts thereof and a label, said label comprising a printed statement which informs a prospective user that dronedarone or pharmaceutically acceptable salts thereof is contraindicated in patients with severe heart failure.

In some embodiments, the printed statement informs a prospective user of one or more of the following:

a) that dronedarone or pharmaceutically acceptable salts thereof is contraindicated in patients with severe heart failure indicated by a history of, or current symptoms of congestive heart failure;

b) that dronedarone or pharmaceutically acceptable salts thereof is contraindicated in patients with severe heart failure indicated by symptoms of heart failure with minimal exertion within the last month;

c) that dronedarone or pharmaceutically acceptable salts thereof is contraindicated in patients with severe heart failure indicated by hospitalization for heart failure within the last month;

d) that dronedarone or pharmaceutically acceptable salts thereof is contraindicated in patients with severe heart failure indicated by NYHA Class IV;

e) that dronedarone or pharmaceutically acceptable salts thereof is contraindicated in patients with severe heart failure indicated by NYHA Class III within the last month;

f) that dronedarone or pharmaceutically acceptable salts thereof is contraindicated in patients with severe heart failure indicated by recent decompensation as indicated by the need for hospitalization or intravenous therapy, for example intravenous inotropic or diuretic therapy; and g) dronedarone or pharmaceutically acceptable salts thereof is contraindicated in patients who were hospitalized for heart failure with recent decompensation requiring hospitalization or intravenous therapy for the treatment of heart failure.

The invention also relates to a package comprising dronedarone or a pharmaceutically acceptable salt thereof and a label, said label comprising at least one message selected from the group consisting of:

a) a primary endpoint of a study of dronedarone, or a pharmaceutically acceptable salt thereof, was the time to first hospitalization for cardiovascular reasons or death from any cause; and b) a secondary endpoint of a study of dronedarone, or pharmaceutically acceptable salt thereof, was death from any cause;

c) a secondary endpoint of a study of dronedarone, or a pharmaceutically acceptable salt thereof, was time to death from any cause;

d) a secondary endpoint of a study of dronedarone, or a pharmaceutically acceptable salt thereof, was time to cardiovascular death;

e) a secondary endpoint of a study of dronedarone, or a pharmaceutically acceptable salt thereof, was time to first hospitalization for cardiovascular reasons;

f) a secondary endpoint of a study of dronedarone, or a pharmaceutically acceptable salt thereof, was time to first hospitalization for atrial fibrillation and other supraventricular rhythm disorders;

g) a secondary endpoint of a study of dronedarone, or a pharmaceutically acceptable salt thereof, was time to first hospitalization for worsening heart failure;

h) a secondary endpoint of a study of dronedarone, or a pharmaceutically acceptable salt thereof, was time to first hospitalization for myocardial infarction;

i) a secondary endpoint of a study of dronedarone, or a pharmaceutically acceptable salt thereof, was time to first hospitalization for myocardial infarction;

j) a secondary endpoint of a study of dronedarone, or a pharmaceutically acceptable salt thereof, was time to first hospitalization for transient ischemic event or cerebral stroke; and k) a secondary endpoint of a study of dronedarone, or a pharmaceutically acceptable salt thereof, was time to sudden death, l) dronedarone, or a pharmaceutically acceptable salt thereof, reduced the combined endpoint of cardiovascular hospitalization or death from any cause by about 24 percent;

m) dronedarone, or a pharmaceutically acceptable salt thereof, reduced the combined endpoint of cardiovascular hospitalization or death from any cause by 24.2 percent;

n) dronedarone, or a pharmaceutically acceptable salt thereof, reduced the combined endpoint of cardiovascular hospitalization or death from any cause by 24.2 percent, driven by a reduction in cardiovascular hospitalization; and o) 70 percent of patients enrolled in a study of dronedarone, or a pharmaceutically acceptable salt thereof, had no heart failure.

Another method of the invention comprises treating a patient with a recent history of or current atrial fibrillation or flutter, said method comprising administrating to said patient a therapeutically effective amount of dronedarone, or a pharmaceutically acceptable salt thereof, wherein said patient does not have severe heart failure.

In one embodiment, the patient does not have severe heart failure, wherein severe heart failure is indicated by one or more selected from the group consisting of:
a) history of, or current symptoms of congestive heart failure at rest;
b) symptoms of heart failure with minimal exertion within the last month; and
c) hospitalization for heart failure within the last month,
d) NYHA Class IV,
e) NYHA Class III within the last month,
f) recent decompensation as indicated by the need for hospitalization or intravenous therapy, for example intravenous inotropic or diuretic therapy,
g) recent decompensation requiring hospitalization or intravenous therapy for the treatment of heart failure.

Another method of the invention relates to transforming a patient with a recent history of or current atrial fibrillation or flutter by decreasing the patient's risk of cardiovascular hospitalizations or mortality, comprising administrating to said patient a therapeutically effective amount of dronedarone, or a pharmaceutically acceptable salt thereof, wherein said patient does not have severe heart failure.

A subject of the invention is a method of decreasing the risk of cardiovascular hospitalizations or mortality in a patient having a history of atrial fibrillation or atrial flutter, said method comprising administering dronedarone, or a pharmaceutically acceptable salt thereof, twice a day with a meal to a patient in need thereof, wherein said patient does not have severe heart failure.

In terms of clinical study, the prevention of "cardiovascular hospitalizations or of mortality" or of "cardiovascular hospitalizations or of cardiovascular mortality" or of "cardiovascular hospitalizations or of sudden death" constitute what are referred to as composite criteria or a combined endpoint.

All the percentages given above correspond to average values.

Diuretics are widely prescribed for their efficacy in the treatment of a diversity of conditions, such as arterial hypertension, congestive heart failure, renal insufficiency, nephrotic syndrome, cirrhosis or glaucoma.

One of the major consequences of a treatment based on diuretics, except for potassium sparing diuretics, is increased potassium excretion which can result in hypokalaemia.

Now, hypokalaemia is known to increase cardiac excitability, resulting, in certain patients, in ventricular arrhythmia and sudden death (Cooper et al., Circulation, 1999, 100, pages 1311-1315).

Advantageously, a subject of the present invention is also the use of dronedarone or a pharmaceutically acceptable salt thereof, for the preparation of a medicament for use in the prevention of cardiovascular hospitalizations and/or of mortality in patients having a history of atrial fibrillation or atrial flutter and receiving a diuretic-based treatment, in particular a treatment based on non-potassium sparing diuretics.

A subject of the present invention is also the use of dronedarone or a pharmaceutically acceptable salt thereof, for the preparation of a medicament for regulating the potassium level in the blood, in particular for use in the prevention of hypokalaemia, especially in patients having histories of atrial fibrillation or atrial flutter and/or patients receiving a diuretic-based treatment, in particular a treatment based on non-potassium sparing diuretics.

Said diuretic is administered at therapeutically active doses chosen between 1 mg/day and 2 g/day.

Among the pharmaceutically acceptable salts of dronedarone, mention may be made of the hydrochloride.

The term "non-potassium sparing diuretic" is intended to mean a diuretic which increases potassium excretion.

The term "cardiovascular hospitalization" means a hospitalization which is caused by at least one of the following pathologies (Hohnloser et al., Journal of cardiovascular electrophysiology, January 2008, vol. 19, No. 1, pages 69-73):
relating to atherosclerosis,
myocardial infarction or unstable angina pectoris,
stable angina pectoris or atypical thoracic pain,
syncope,
transient ischemic event or cerebral stroke (except intracranial haemorrhage),
atrial fibrillation and other supraventricular rhythm disorders,
non-fatal cardiac arrest,
ventricular arrhythmia,
cardiovascular surgery, except heart transplant,
heart transplant,
implantation of a cardiac stimulator (pacemaker), of an implantable defibrillator ("ICD") or of another cardiac device,
percutaneous coronary, cerebrovascular or peripheral intervention,
variations in arterial pressure (hypotension, hypertension, except syncope),
cardiovascular infection,
major bleeding/haemorrhage (requiring two or more blood cell pellets or any intracranial haemorrhage),
pulmonary embolism or deep vein thrombosis,
worsening of congestive heart failure including acute pulmonary oedema or dyspnoea from cardiac causes.

Consequently, the prevention of cardiovascular hospitalization may be understood as the prevention of cardiovascular hospitalization for at least one of the above mentioned pathologies.

Mention may be made of the prevention of cardiovascular hospitalization for atrial fibrillation and/or other supraventricular rhythm disorders.

Mention may also be made of the prevention of cardiovascular hospitalization for transient ischemic event or cerebral stroke.

Thus, a subject of the present invention is also the use of dronedarone or a pharmaceutically acceptable salt thereof, for the preparation of a medicament for the prevention of cardiovascular hospitalization for at least one of the above mentioned pathologies such as atrial fibrillation and/or other supraventricular rhythm disorders and/or stroke.

The term "mortality" or "death" are equivalent and cover mortality due to any cause, whether cardiovascular or non-cardiovascular or unknown.

The term "cardiovascular mortality" covers, in the context of the invention, mortality due to any cardiovascular causes (any death except those due to a non-cardiovascular cause), in particular death from an arrhythmic cause, also called arrhythmic death, and more particularly, sudden death from cardiovascular causes, also called sudden death or sudden cardiac death.

Cardiovascular mortality may be due for example to:
  Aortic dissection/aneurysm
  Cardiac tamponade
  Cardiogenic shock
  congestive heart failure
  Death during a cardiovascular transcutaneous interventional procedure or cardiovascular surgical intervention
  Hemorrhage (except cardiac tamponade)
  Myocardial infarction or unstable angina (including complications of myocardial infarction, except arrhythmias)
  Pulmonary or peripheral embolism
  Stroke
  Sudden cardiac death (e.g., unwitnessed death or documented asystole)
  Ventricular arrhythmia, subclassified as torsades de pointes, ventricular extrasystole, ventricular fibrillation, ventricular tachycardia (non-sustained and sustained ventricular tachycardia), or other ventricular arrhythmia
  Unknown cause The term "sudden death" refers, in general, to death occurring within the hour or less than one hour after the appearance of new symptoms or unexpected death without warning.

It will also be specified that the expression "patients having a history of atrial fibrillation or atrial flutter", "patients with a history of or a current atrial fibrillation or flutter" or "patients with a recent history of or a current atrial fibrillation or flutter" or "patients with paroxysmal or persistent atrial fibrillation or flutter" or "patients with a history of, or a current paroxysmal or persistent atrial fibrillation or flutter" or "patients with a recent history of, or a current paroxysmal or persistent atrial fibrillation or flutter" or "patients with paroxysmal or intermittent atrial fibrillation or atrial flutter and a recent episode of atrial fibrillation or atrial flutter, who are in sinus rhythm or who will be cardioverted" or "patients with paroxysmal or persistent atrial fibrillation or atrial flutter and a recent episode of atrial fibrillation or atrial flutter, who are in sinus rhythm or who will be cardioverted" means a patient who, in the past, has presented one or more episodes of atrial fibrillation or flutter and/or who is suffering from atrial fibrillation or atrial flutter at the time the dronedarone or a pharmaceutically acceptable salt thereof is used. More particularly, this expression means patients with documentation of having been in both atrial fibrillation or flutter and sinus rhythm within the last 6 months preceding the start of treatment. Patients could be either in sinus rhythm, or in atrial fibrillation or flutter at the time the dronedarone or a pharmaceutically acceptable salt thereof is initiated.

It will also be specified that the terms "persistent" and "intermittent" are equivalent.

Patients in "permanent atrial fibrillation or flutter" are patients that have all scheduled ECGs in this rhythm throughout the period the dronedarone or a pharmaceutically acceptable salt thereof is administered.

The term "coronary disease" or "coronary heart disease" refers to:
  1) Coronary artery disease: documented history of acute myocardial infarction and/or significant ($\geq$70%) coronary artery stenosis and/or history of a revascularization procedure (percutaneous transluminal coronary angioplasty, stent implantation in a coronary artery, coronary artery bypass graft, etc) and/or a positive exercise test and/or positive nuclear scan of cardiac perfusion
  2) Ischemic dilated cardiomyopathy: clinically significant left ventricular dilatation secondary to coronary artery disease Of course, it may be understood that "prevention of cardiovascular hospitalization and/or mortality" results in the reduction of the risk of cardiovascular hospitalization and or mortality or in the reduction of the need of cardiovascular hospitalization and or mortality.

Among the patients with a recent history of, or a current atrial fibrillation or atrial flutter, mention may be made of patients with a recent history of, or a current, non permanent atrial fibrillation or flutter.

Among the patients, notably patients having a history of atrial fibrillation or atrial flutter, mention may also be made of patients also exhibiting at least one of the following risk factors:
  age notably equal to or above 70, or even above 75,
  hypertension,
  diabetes,
  history of cerebral stroke or of systemic embolism, i.e. prior cerebrovascular accident,
  left atrial diameter greater than or equal to 50 mm measured for example by echocardiography,
  left ventricular ejection fraction less than 40%, measured for example by two-dimensional echography.

The efficacy of dronedarone to reduce cardiovascular hospitalization or death is now clinically proven in patients with the above mentioned associated risk factors.

The above mentioned risks factors may be defined as cardiovascular risk factors which are associated to atrial fibrillation.

Among the patients, notably patients having a history of atrial fibrillation or atrial flutter, mention may also be made of patients also exhibiting additional risk factors, i.e. at least one of the following pathologies:
  hypertension,
  underlying structural heart disease,
  tachycardia,
  coronary disease,
  non-rheumatic heart valve disease,
  dilated cardiomyopathy of ischemic origin,
  ablation of atrial fibrillation or flutter, for example catheter ablation or endomyocardial ablation,
  supraventricular tachycardia other than atrial fibrillation or flutter,
  history of heart valve surgery,
  non-ischemic dilated cardiomyopathy,
  hypertrophic cardiomyopathy,
  rheumatic valve disease,
  sustained ventricular tachycardia,
  congenital cardiopathy,
  ablation, for example catheter ablation, for tachycardia other than for atrial fibrillation or flutter,
  ventricular fibrillation,
and/or at least one cardiac device chosen from:
  a cardiac stimulator,
  an implantable defibrillator ("ICD").

The expression "regulating the potassium level in the blood" means preventing the decrease or a possible increase in said level.

The principal classes of non-potassium sparing diuretics are:
thiazide diuretics,
loop diuretics,
proximal diuretics (osmotics, carbonic anhydrase inhibitors).

For their therapeutic use, dronedarone and pharmaceutically acceptable salts thereof are generally introduced into pharmaceutical compositions.

These pharmaceutical compositions contain an effective dose of dronedarone or of a pharmaceutically acceptable salt thereof, and also at least one pharmaceutically acceptable excipient.

Said pharmaceutical composition may be given once or twice a day with food.

The dose of dronedarone administered per day, orally, may reach 800 mg, taken in one or more intakes, for example one or two.

More specifically, the dose of dronedarone administered may be taken with food.

More specifically, the dose of dronedarone administered per day, orally, may reach 800 mg, taken in two intakes with a meal.

The dose of dronedarone administered per day, orally may be taken at a rate of twice a day with a meal for example with the morning and the evening meal.

More specifically, the two intakes may comprise same quantity of dronedarone.

There may be specific cases where higher or lower dosages are appropriate; such dosages do not depart from the context of the invention. According to the usual practice, the dosage appropriate for each patient is determined by the physician according to the method of administration, the weight, the pathology, the body surface, the cardiac output and the response of said patient.

Said excipients are chosen according to the pharmaceutical form and the method of administration desired, from the usual excipients which are known to those skilled in the art.

In said pharmaceutical compositions for oral, sublingual, subcutaneous, intramuscular, intravenous, topical, local, intratracheal, intranasal, transdermal or rectal administration, dronedarone, or the salt thereof, can be administered in unit administration form, as a mixture with conventional pharmaceutical excipients, to animals and to humans in the cases mentioned above.

The suitable unit administration forms comprise forms for oral administration, such as tablets, soft or hard gel capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, dronedarone and pharmaceutically acceptable salts thereof can be used in creams, gels, ointments or lotions.

By way of example, a unit administration form of dronedarone or a pharmaceutically acceptable salt thereof, in tablet form, may correspond to one of the following examples:

| Ingredients | mg | % |
|---|---|---|
| Dronedarone hydrochloride (corresponding to 400 mg of base) | 426 | 65.5 |
| Methylhydroxypropylcellulose | 21.1 | 3.25 |
| Lactose monohydrate | 46.55 | 7.2 |
| Maize starch | 45.5 | 7 |
| Polyvinylpyrrolidone | 65 | 10 |
| Poloxamer 407 | 40 | 6.15 |
| Anhydrous colloidal silica | 2.6 | 0.4 |
| Magnesium stearate | 3.25 | 0.5 |
| | 650 | 100 |

| Ingredients | mg | % |
|---|---|---|
| Dronedarone hydrochloride (corresponding to 400 mg of base) | 426 | 65.5 |
| Microcrystalline cellulose | 65 | 10 |
| Anhydrous colloidal silica | 2.6 | 0.4 |
| Anhydrous lactose | 42.65 | 6.6 |
| Polyvinylpyrrolidone | 13 | 2 |
| Poloxamer 407 | 40 | 6.15 |
| Macrogol 6000 | 57.5 | 8.85 |
| Magnesium stearate | 3.25 | 0.5 |
| | 650 | 100 |

| Ingredients | mg |
|---|---|
| Dronedarone hydrochloride (corresponding to 400 mg of base) | 426 |
| Microcrystalline cellulose | 26 |
| Maize starch | 45.5 |
| Polyvinylpyrrolidone | 65 |
| Poloxamer 407 | 40 |
| Anhydrous colloidal silica | 3.25 |
| Magnesium stearate | 3.25 |
| Lactose monohydrate | 41.65 |
| | 650 |

| Ingredients | mg |
|---|---|
| Dronedarone hydrochloride (corresponding to 400 mg of base) | 213 |
| Microcrystalline cellulose | 13 |
| Maize starch | 22.75 |
| Polyvinylpyrrolidone | 32.5 |
| Poloxamer 407 | 20 |
| Anhydrous colloidal silica | 1.3 |
| Magnesium stearate | 1.625 |
| Lactose monohydrate | 20.825 |
| | 650 |

According to another of its aspects, the present invention also relates to a method for treating the pathologies indicated above, which comprises the administration, to a patient, of an effective dose of dronedarone or a pharmaceutically acceptable salt thereof.

One method of the invention includes decreasing the risk of mortality, cardiac hospitalizations, or the combination thereof in a patient, said method comprising administering to said patient an effective amount of dronedarone or a pharmaceutically acceptable salt thereof, with food.

In one embodiment, the mortality is a cardiovascular mortality. In one embodiment, the mortality is a sudden death.

Another method of the invention is a method of regulating the potassium level in the blood of a patient having a history of or current atrial fibrillation or atrial flutter, said method comprising administering to said patient dronedarone or a pharmaceutically acceptable salt thereof, with food.

In some embodiments of the above methods according to the invention, the patient has a history of or current atrial fibrillation or flutter. In some embodiments of the above methods according to the invention, the patient has a recent history of or a current paroxysmal or persistent atrial fibrillation or atrial flutter. In some embodiments of the above methods according to the invention, the patient has a history of or a current, non permanent atrial fibrillation or atrial flutter. In some embodiments of the above methods according to the invention, the administration of dronedarone or pharmaceutically acceptable salt thereof prevents cardiovascular hospitalizations. In some embodiments of the above methods according to the invention, said patient has a permanent atrial fibrillation or atrial flutter. In some embodiments of the above methods according to the invention, said patient has structural heart disease. In some embodiments of the above methods according to the invention, said patient has congestive heart failure in a stable hemodynamic condition. In some embodiments of the above methods according to the invention, said patient has congestive heart failure defined as NYHA class III in a stable hemodynamic condition. In some embodiments of the above methods according to the invention, said patient has congestive heart failure defined by a reduced left ventricular ejection fraction below 0.35 in a stable hemodynamic condition. In some embodiments of the above methods according to the invention, said patient also exhibits one or more of the above mentioned associated risk factors.

Another method of the invention is a method of preventing coronary disease in a patient with a history of or current atrial fibrillation or atrial flutter, said method comprising administrating to said patient a therapeutically effective amount of dronedarone or a pharmaceutically acceptable salt thereof. In one embodiment, said patient further receives a diuretic-based treatment. In one embodiment, said patient further receives a treatment with a non-potassium-sparing diuretic. In some embodiments, said patient also exhibits one or more of the above mentioned associated risk factors.

BRIEF DESCRIPTION OF THE DRAWINGS

The present invention is illustrated by the data hereinafter with reference to the attached drawings in which.

Figure 1:
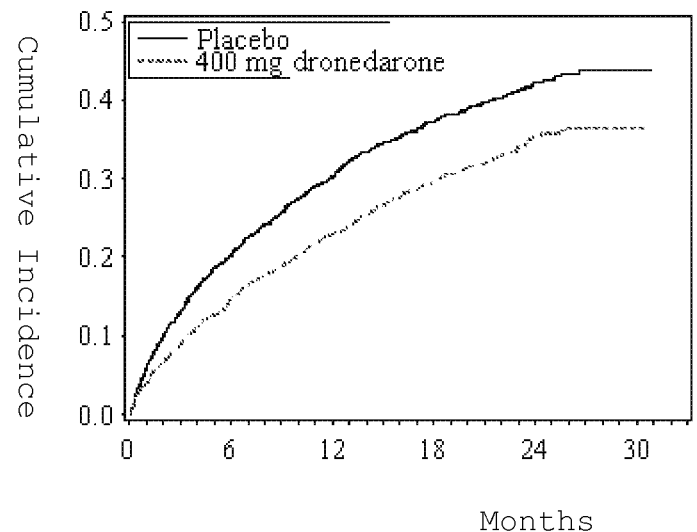
FIG. 1 represents a Kaplan Meier curve with the cumulative rate of hospitalization or of death from any cause over a period of 30 months.

The efficacy, relative to a placebo, of dronedarone and of pharmaceutically acceptable salts thereof, in the prevention of cardiovascular hospitalizations or of mortality was demonstrated, by means of dronedarone hydrochloride, in a prospective, multinational, multicentre, double-blind clinical study with random distribution in two groups of treatment (group treated with dronedarone hydrochloride and group treated with a placebo) of patients having a history of atrial fibrillation or atrial flutter.

I. Patient Selection

The patients had to have a history of atrial fibrillation or flutter and/or could be in normal sinus rhythm or in atrial fibrillation or flutter at inclusion.

The patient recruitment was carried out by taking into account the following inclusion criteria:

Inclusion Criteria:
1) One of the following risk factors had to be present:
    age equal to or greater than 70 years,
    hypertension (taking antihypertensives of at least two different classes),
    diabetes,
    history of cerebral stroke (transient ischemic event or completed cerebral stroke) or of systemic embolism,
    left atrial diameter greater than or equal to 50 mm measured by echocardiography,
    left ventricular ejection fraction less than 40%, measured by two-dimensional echography;
or
    age equal to or above 70, or even above 75, possibly combined with at least one of the risk factors below:
    hypertension (taking antihypertensives of at least two different classes),
    diabetes,
    history of cerebral stroke (transient ischemic event or completed cerebral stroke) or of systemic embolism,
    left atrial diameter greater than or equal to 50 mm measured by echocardiography,
    left ventricular ejection fraction less than 40%, measured by two-dimensional echography;
2) availability of an electrocardiogram carried out during the past 6 months in order to document the presence or the history of atrial fibrillation or flutter;
3) availability of an electrocardiogram carried out during the past 6 months in order to document the presence or absence of normal sinus rhythm.

Exclusion Criteria:

General Criteria:
    Refusal or inability to give informed consent to participate in the study.
    Any non cardiovascular illness or disorder that could preclude participation or severely limit survival including cancer with metastasis and organ transplantation requiring immune suppression.
    Pregnant women (pregnancy test must be negative) or women or childbearing potential not on adequate birth control: only women with a highly effective method of contraception [oral] contraception or intra-uterine device (IUD) or sterile can be randomize.

Breastfeeding women.

Previous (2 preceding months) or current participation in another trial with an investigational drug (under development) or with an investigational device.

Previous participation in this trial.

Criteria Related to a Cardiac Condition:

Patients in permanent atrial fibrillation

Patients in unstable hemodynamic condition such as acute pulmonary edema within 12 hours prior to start of study medication; cardiogenic shock; treatment with IV pressor agents; patients on respirator; congestive heart failure of stage NYHA IV within the last 4 weeks; uncorrected, hemodynamically significant primary obstructive valvular disease; hemodynamically significant obstructive cardiomyopathy; a cardiac operation or revascularization procedure within 4 weeks preceding randomization Planned major non-cardiac or cardiac surgery or procedures including surgery for valvular heart disease, coronary artery bypass graft (CABG), percutaneous coronary intervention (PCI), or on urgent cardiac transplantation list Acute myocarditis or constrictive pericarditis Bradycardia<50 bpm and/or PR-interval$\geq$0.28 sec on the last 12-lead ECG.

Significant sinus node disease (documented pause of 3 seconds or more) or $2^{nd}$ or $3^{rd}$ degree atrioventricular block (AV-block) unless treated with a pacemaker.

Criteria Related to Concomitant Medications:

Need of a concomitant medication that is prohibited in this trial, including the requirement for Vaughan Williams Class I and III anti-arrhythmic drugs, that would preclude the use of study drug during the planned study period, i.e. patients have to stop others antiarrhythmics such as Vaughan Williams Class I and III anti-arrhythmic drugs, for example amiodarone, flecainide, propafenone, quinidine, disopyramide, dofetilide, solatol.

Criteria Related to Laboratory Abnormalities:

Plasma potassium<3.5 mmol/l (as anti-arrhythmic drugs can be arrhythmogenic in patients with hypokalemia, this must be corrected prior to randomization.

A calculated GFR at baseline<10 ml/min using the Cockroft Gault formula (GFR [ml/min]=(140−AGE [years]*WEIGHT [kilograms]*CONSTANT/CREATININE [μmol/L], where CONSTANT is 1 for men and 0.85 for women).

Furthermore, the concomitant use of grapefruit juice and all potent inhibitors of CYP3A4 such as ketoconazole were prohibited.

II. Duration and Treatment

Treatment was initiated using tablets containing either the placebo or an amount of dronedarone hydrochloride corresponding to 400 mg of dronedarone at a rate of twice a day with the morning and evening meal and more specifically at a rate of one tablet in the morning during or shortly after breakfast and one tablet in the evening during or shortly after dinner.

The anticipated duration of the treatment was variable according to the time at which each patient was included in the study, and could range from a minimum of 12 months for the last patient included up to a maximum corresponding to the entire duration of the study (12 months+duration of inclusion), i.e. approximately 30 months for the first patients included.

III. Results

The results obtained in this trial were analysed by the Kaplan Meier method for the figures, and the relative risk (RR) was estimated using Cox's proportional-effect regression model.

The relative risk (RR) is the ratio of the rates of occurrence of a hospitalization or of a death among the patients on dronedarone, relative to the patients on placebo.

The percentage reduction x of a given event (hospitalization, death, cardiovascular death, etc.) is calculated in the following way:

$$x = 1 - \text{relative risk}.$$

III.1. Results Relating to Cardiovascular Hospitalizations and to Mortality (Principal Judgement Criterion)

Among the 4628 patients included in the study, 2301 were part of the group treated with dronedarone hydrochloride.

917 events were recorded in the placebo group, against 734 in the group treated with dronedarone hydrochloride.

The calculated relative risk is 0.758 with a $p=2\times10^{-8}$, i.e. a reduction in cardiovascular hospitalizations and deaths of 24.2% on dronedarone hydrochloride, the result being highly significant.

FIG. 1, which reproduces the results obtained, shows a clear separation of the two cumulative curves very soon after the beginning of the treatment, this separation persisting over time throughout the duration of the study.

III.2. Results Relating to Cardiovascular Hospitalizations and to Cardiovascular Mortality Among the 4628 patients included in the study, 2301 were part of the group treated with dronedarone hydrochloride.

892 events were recorded in the placebo group, against 701 in the group treated with dronedarone hydrochloride.

The calculated relative risk is 0.745 with a $p=45\times10^{-10}$, i.e. a reduction in cardiovascular hospitalizations and cardiovascular deaths of 25.5% on dronedarone hydrochloride, the result being highly significant.

Figure 2:
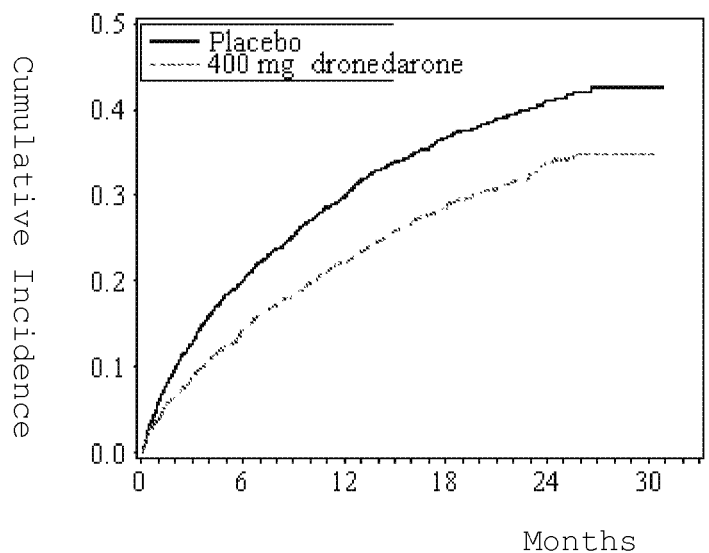
FIG. 2 represents a Kaplan Meier curve with the cumulative rate of hospitalization or of cardiovascular death over a period of 30 months.

FIG. 2, which reproduces the results obtained, shows a clear separation of the two cumulative curves very soon after the beginning of the treatment, this separation persisting over time throughout the duration of the study.

III.3. Results Relating to Cardiovascular Hospitalizations and to Sudden Death

Among the 4628 patients included in the study, 2301 were part of the group treated with dronedarone hydrochloride.

873 events were recorded in the placebo group, against 684 in the group treated with dronedarone hydrochloride.

The calculated relative risk is 0.743 with a $p=48\times10^{-10}$, i.e. a reduction in cardiovascular hospitalizations and sudden deaths of 25.5% on dronedarone hydrochloride, the result being highly significant.

Figure 3:
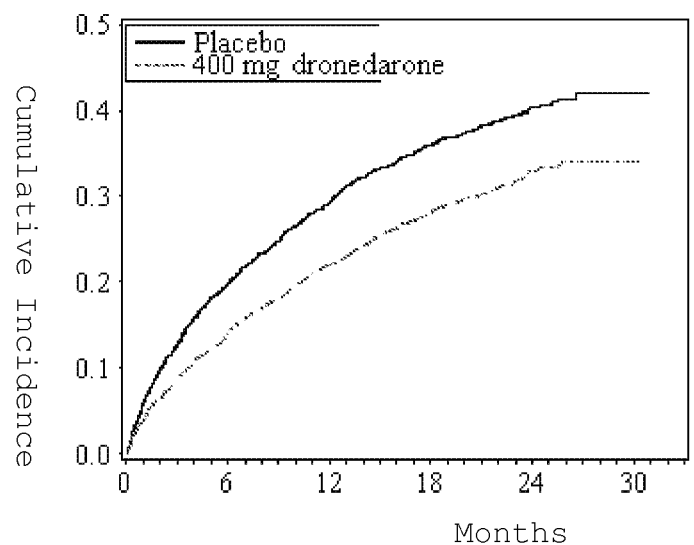
FIG. 3 represents a Kaplan Meier curve with the cumulative rate of hospitalization or of sudden death over a period of 30 months.

FIG. 3, which reproduces the results obtained, shows a clear separation of the two cumulative curves very soon after the beginning of the treatment, this separation persisting over time throughout the duration of the study.

III.4. Results Relating to Cardiovascular Hospitalizations

Among the 4628 patients included in the study, 2301 were part of the group treated with dronedarone hydrochloride.

859 events were recorded in the placebo group, against 675 in the group treated with dronedarone hydrochloride.

The calculated relative risk is 0.745 with a $p=9\times10^{-9}$, i.e. a reduction in cardiovascular hospitalizations of 25.5% on dronedarone hydrochloride.

Figure 4:
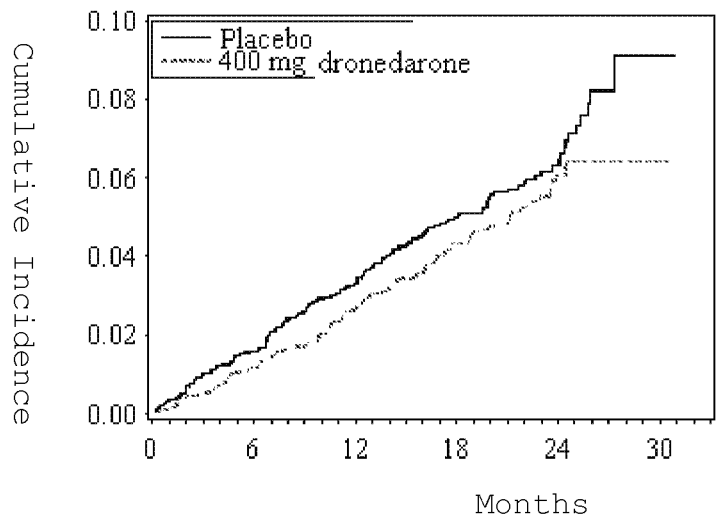
FIG. 4 represents a Kaplan Meier curve with the cumulative rate of hospitalization over a period of 30 months.

FIG. 4, which reproduces the results obtained, shows a clear separation of the two cumulative curves very soon after the beginning of the treatment, this separation persisting over time throughout the duration of the study.

III.5. Results Relating to Cardiovascular Hospitalizations for Atrial Fibrillation or Supraventricular Arrhythmia Among the 4628 patients included in the study, 2301 were part of the group treated with dronedarone hydrochloride.

457 events were recorded in the placebo group, against 296 in the group treated with dronedarone hydrochloride.

The calculated relative risk is 0.616, i.e. a reduction in cardiovascular hospitalizations for atrial fibrillation of 38.4%

III.6. Results Relating to Cardiovascular Hospitalizations for Transient Ischemic Event or Stroke Among the 4628 patients included in the study, 2301 were part of the group treated with dronedarone hydrochloride.

61 events were recorded in the placebo group, against 43 in the group treated with dronedarone hydrochloride.

The calculated relative risk is 0.66 with a p=0.027, i.e. a reduction in cardiovascular hospitalizations for transient ischemic event or stroke of 34% on dronedarone hydrochloride.

III.7. Results Relating to Mortality from any Cause

Among the 4628 patients included in the study, 2301 were part of the group treated with dronedarone hydrochloride.

139 deaths were recorded in the placebo group, against 116 in the group treated with dronedarone hydrochloride.

The calculated relative risk is 0.844 with a p=0.1758, i.e. a reduction of death of 15.6% on dronedarone hydrochloride.

Figure 5:
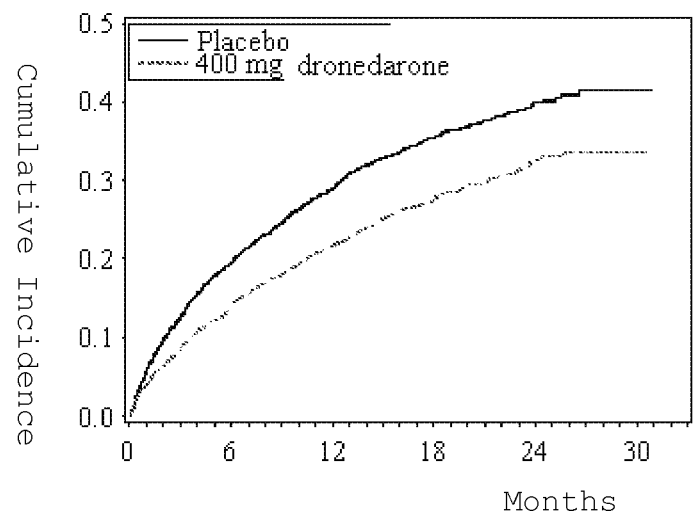
FIG. 5 represents a Kaplan Meier curve with the cumulative rate of death from any cause over a period of 30 months.

FIG. 5, which reproduces the results obtained, shows a clear separation of the two cumulative curves very soon after the beginning of the treatment, this separation persisting over time throughout the duration of the study.

III.8. Results Relating to Cardiovascular Mortality

Among the 4628 patients included in the study, 2301 were part of the group treated with dronedarone hydrochloride.

94 cardiovascular deaths were recorded in the placebo group, against 65 in the group treated with dronedarone hydrochloride.

The calculated relative risk is 0.698 with a p=0.0252, i.e. a reduction in cardiovascular mortality of 30.2% on dronedarone hydrochloride.

Figure 6:
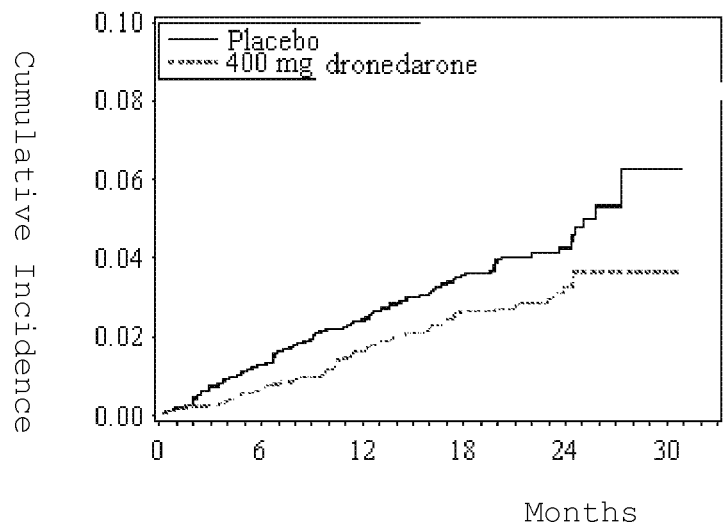
FIG. 6 represents a Kaplan Meier curve with the cumulative rate of cardiovascular death over a period of 30 months.

FIG. 6, which reproduces the results obtained, shows a clear separation of the two cumulative curves very soon after the beginning of the treatment, this separation persisting over time throughout the duration of the study.

III.9. Results Relating to Arrhythmic Death

Among the 4628 patients included in the study, 2301 were part of the group treated with dronedarone hydrochloride.

48 arrhythmic deaths (deaths from cardiac arrhythmia) were recorded in the placebo group, against 26 in the group treated with dronedarone hydrochloride.

The calculated relative risk is 0.55 with a p=0.001, i.e. a reduction of arrhythmic death of 45% on dronedarone hydrochloride.

III.10. Results Relating to Sudden Death

Among the 4628 patients included in the study, 2301 were part of the group treated with dronedarone hydrochloride.

35 sudden deaths were recorded in the placebo group, against 14 in the group treated with dronedarone hydrochloride.

The calculated relative risk is 0.405 with a p=0.0031, i.e. a reduction in sudden death of 59.5% on dronedarone hydrochloride.

Figure 7:
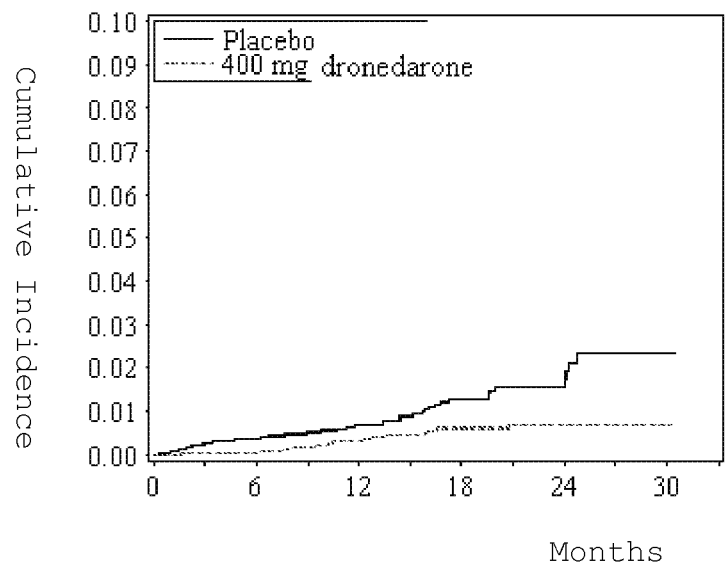
FIG. 7 represents a Kaplan Meier curve with the cumulative rate of sudden death over a period of 30 months.

FIG. 7, which reproduces the results obtained, shows a clear separation of the two cumulative curves very soon after the beginning of the treatment, this separation persisting over time throughout the duration of the study.

III.11. Regulation of the Blood Potassium Level

The potassium concentration-modulating effect is clearly documented in the study by virtue of the results of analyses of regular blood samples taken throughout the duration of the study in the context of the monitoring of vital parameters.

Figure 8:
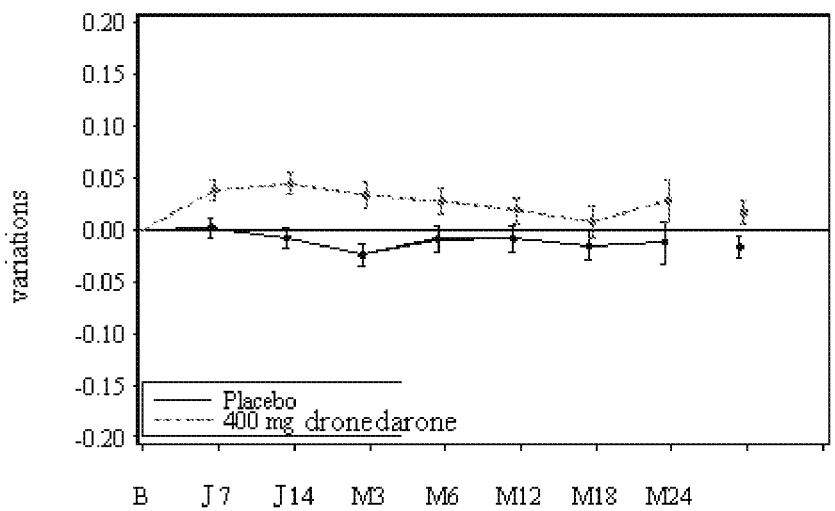
FIG. 8 represents the mean variations in potassium between the first and the last administration over a period of 30 months.

The variations in potassium (in mmol/l) between the first and the last administration of the medicament of the study are included in FIG. 8, in which B signifies basal level, D signifies day and M signifies month.

An analysis of covariance of the change in blood potassium level, taking into account the starting value during the study after the $24^{th}$ month, shows a significant different in favour of dronedarone compared to the placebo (p<0.0001).

Dronedarone therefore makes it possible to regulate the potassium level in the blood.

III.12. Results Relating to the Patients in the Study Receiving in Addition a Diuretic-Based Treatment The clinical results of the study corroborate the hypothesis that modulating potassium decreases the risk of sudden death, in particular in patients exposed to the risk of a decrease in potassium exacerbated by the administration of a diuretic treatment: the reduction in the risk of sudden death by dronedarone, i.e. the prevention of sudden death compared with the placebo, was 70.4% in the patients on diuretics and 34% in the patients not taking diuretics.

Furthermore, the reduction in the risk was greater in the groups of patients liable to be treated with diuretics, such as hypertensive patients, where the reduction in the risk was 62%, against a reduction of 45.5% observed in the patients who were not hypertensive.

III.13. Results Relating to Cardiovascular Hospitalizations and to Mortality in Patients Who Developed "Permanent Atrial Fibrillation/Flutter"

Among the 4628 patients included in the study, 2301 were part of the group treated with dronedarone hydrochloride.

294 patients who developed permanent atrial fibrillation/flutter in the group treated with placebo versus 178 patients in the group treated with dronedarone hydrochloride (p<0.001).

74 events were recorded in the placebo group versus 29 in the group treated with dronedarone hydrochloride.

The calculated relative risk is 0.67 with a p=0.06, i.e. a reduction in cardiovascular hospitalizations and to mortality in patients with permanent atrial fibrillation/flutter of 33% on dronedarone hydrochloride.

Figure 9:
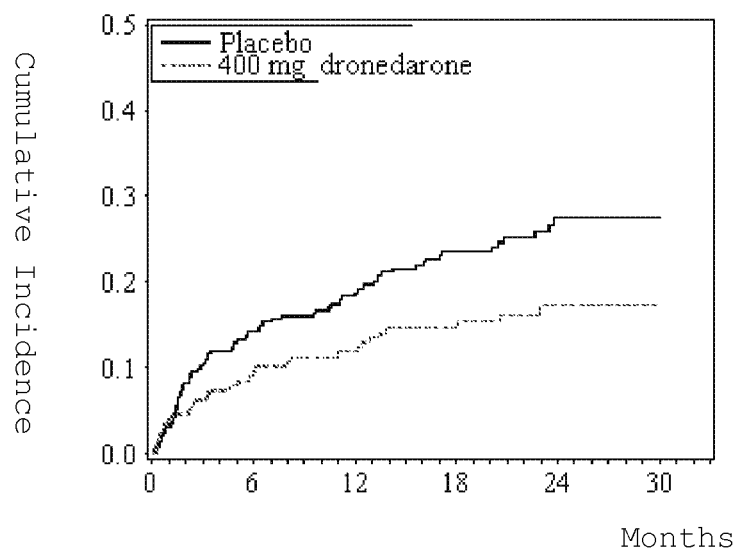
FIG. 9 represents a Kaplan Meier curve with the cumulative rate of hospitalization or of death from any cause over a period of 30 months.

FIG. 9, which reproduces the results obtained, shows a clear separation of the two cumulative curves very soon after the beginning of the treatment, this separation persisting over time throughout the duration of the study.

III.14. Results Relating to the Prevention of Cardiovascular Hospitalization or Death in Patients with a Structural Heart Disease From the 4628 patients included in the trial, 2301 were part of the group treated with dronedarone hydrochloride.

629 events were reported in the placebo group versus 486 in the group treated with dronedarone hydrochloride.

Calculated relative risk was equal to 0.76, i.e. a decrease of cardiovascular hospitalization or death of 24%.

III.15. Results Relating to the Prevention of Cardiovascular Hospitalization in Patients with a Structural Heart Disease From the 4628 patients included in the trial, 2301 were part of the group treated with dronedarone hydrochloride.

583 events were reported in the placebo group versus 452 in the group treated with dronedarone hydrochloride.

Calculated relative risk was equal to 0.76, i.e. a decrease of cardiovascular hospitalization of 24%.

III.16. Results Relating to the Prevention of Death in Patients with a Structural Heart Disease From the 4628 patients included in the trial, 2301 were part of the group treated with dronedarone hydrochloride.

106 events were reported in the placebo group versus 77 in the group treated with dronedarone hydrochloride.

Calculated relative risk was equal to 0.76, i.e. a decrease of death of 24%.

III.17. Results Relating to the Prevention of Cardiovascular Death in Patients with a Structural Heart Disease From the 4628 patients included in the trial, 2301 were part of the group treated with dronedarone hydrochloride.

75 events were reported in the placebo group versus 48 in the group treated with dronedarone hydrochloride.

Calculated relative risk was equal to 0.67, i.e. a decrease of cardiovascular deaths of 33%.

III.18. Results Relating to the Prevention of Cardiovascular Hospitalization and Death in Patients with a Congestive Heart Failure Defined as NYHA Class III in a Stable Hemodynamic Condition From the 4628 patients included in the trial, 2301 were part of the group treated with dronedarone hydrochloride.

At randomization, 109 patients with NYHA class III congestive heart failure in a stable hemodynamic condition were part of the placebo group and 91 patients with NYHA class III congestive heart failure in a stable hemodynamic condition were part of the group treated with dronedarone hydrochloride.

71 events were reported in the placebo group versus 40 in the group treated with dronedarone hydrochloride.

Calculated relative risk was equal to 0.56, i.e. a decrease of cardiovascular hospitalization or death of 44%.

Figure 10:
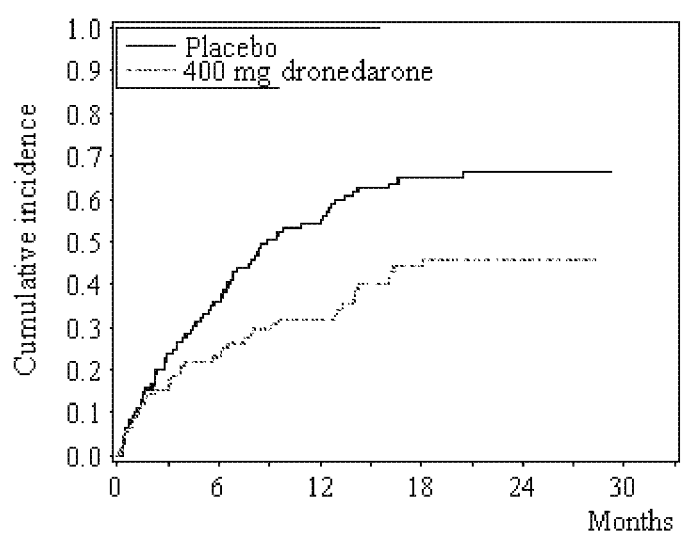
FIG. 10 represents a Kaplan Meier curve with the cumulative rate of hospitalization or of death from any cause in Patients with NYHA class III congestive heart failure over a period of 30 months.

FIG. 10 shows that the effect of dronedarone occurred early and increased over time.

III.19. Results Relating to the Prevention of Cardiovascular Hospitalization and Death in Patients with Congestive Heart Failure Defined with a Reduced Left Ventricular Ejection Fraction Below 0.35 in a Stable Hemodynamic Condition From the 4628 patients included in the trial, 2301 were part of the group treated with dronedarone hydrochloride.

III.20. Results Relating to the Prevention of Death in Patients with Congestive Heart Failure Defined as NYHA Class III From the 4628 patients included in the trial, 2301 were part of the group treated with dronedarone hydrochloride.

At randomization, 109 patients with NYHA class III congestive heart failure in a stable hemodynamic condition were part of the placebo group and 91 patients with NYHA class III congestive heart failure in a stable hemodynamic condition were part of the group treated with dronedarone hydrochloride.

21 events were reported in the placebo group versus 12 in the group treated with dronedarone hydrochloride.

Calculated relative risk was equal to 0.66, i.e. a decrease of death of 34%.

III.21. Results Relating to the Prevention of Death in Patients with Congestive Heart Failure in a Stable Hemodynamic Condition as Defined by a Reduced Left Ventricular Ejection Fraction Below 0.35

From the 4628 patients included in the trial, 2301 were part of the group treated with dronedarone hydrochloride.

At randomization, 87 patients with congestive heart failure in a stable hemodynamic conditions defined by a reduced left ventricular ejection fraction below 0.35 were part of the placebo group and 92 patients with congestive heart failure in a stable hemodynamic condition as defined by a reduced defined with a left ventricular ejection fraction below 0.35 were part of the group treated with dronedarone hydrochloride.

16 events were reported in the placebo group versus 10 in the group treated with dronedarone hydrochloride.

Calculated relative risk was equal to 0.55, i.e. a decrease of death of 45%.

III.22. Results Relating to the Prevention of Death in Patients with Congestive Heart Failure in a Stable Hemodynamic Condition as Defined as NYHA Class III and by a Reduced Left Ventricular Ejection Fraction Below 0.35

|  | Placebo (N = 23) | Dronedarone 400 mg BID (N = 24) |
|---|---|---|
| Number of events, n | 19 | 13 |
| Median survival [95% CI](day) | 254.0 [131.0; 293.0] | 487.0 [182.0; NA] |
| Cumulative incidence of events at 6 months [95% CI] | 0.348 [0.153; 0.542] | 0.292 [0.110; 0.474] |
| Cumulative incidence of events at 1 year [95% CI] | 0.696 [0.508; 0.884] | 0.375 [0.181; 0.569] |
| Cumulative incidence of events at 2 years [95% CI] | 0.837 [0.680; 0.993] | 0.578 [0.368; 0.788] |
| Endpoint's composition: |  |  |
| Cardiovascular hospitalization | 15 | 10 |
| Death from any cause | 4 | 3 |
| Cardiovascular death | 3 | 2 |
| Non cardiovascular death | 1 | 1 |
| Log-rank test p-value | 0.0711 | |
| Relative risk [95% CI]a | 0.523 [0.256; 1.070] | |

At randomization, 87 patients with congestive heart failure in a stable hemodynamic condition as defined by a reduced left ventricular ejection fraction below 0.35 were part of the placebo group and 92 patients with congestive heart failure in a stable hemodynamic condition defined with a reduced left ventricular ejection fraction below 0.35 were part of the group treated with dronedarone hydrochloride.

47 events were reported in the placebo group versus 39 in the group treated with dronedarone hydrochloride.

Calculated relative risk was equal to 0.68, i.e. a decrease of cardiovascular hospitalization or death 32%.

III.23. Results Relating to the Prevention of Hospitalizations Associated with Congestive Heart Failure that is for Patients Who Developed Congestive Heart Failure From the 4628 patients included in the trial, 2301 were part of the group treated with dronedarone hydrochloride.

132 events were reported in the placebo group versus 112 in the group treated with dronedarone hydrochloride.

Calculated relative risk was equal to 0.855, i.e. a decrease of cardiovascular hospitalization associated with congestive heart failure of 14.5%.

III.24. Results Relating to the Prevention of Hospitalizations Associated with Class IV Congestive Heart Failure that is for Patients Who Developed Congestive Heart Failure From the 4628 patients included in the trial, 2301 were part of the group treated with dronedarone hydrochloride.

54 events were reported in the placebo group versus 42 in the group treated with dronedarone hydrochloride.

Calculated relative risk was equal to 0.78, i.e. a decrease of cardiovascular hospitalization associated with class IV congestive heart failure of 22%.

III.25. Results Relating to the Prevention of Cardiovascular Hospitalization or Death in Patients with Coronary Heart Disease From the 4628 patients included in the trial, 2301 were part of the group treated with dronedarone hydrochloride.

At randomization, 737 patients with coronary heart disease were part of the placebo group and 668 patients with coronary heart disease were part of the group treated with dronedarone hydrochloride.

350 events were reported in the placebo group versus 252 in the group treated with dronedarone hydrochloride.

Calculated relative risk was equal to 0.733, i.e. a decrease of cardiovascular hospitalization or death of 27% in patients with coronary heart disease (P=0.0002).

III.26. Results Relating to the Prevention of Cardiovascular Hospitalization for Patients with Coronary Heart Disease From the 4628 patients included in the trial, 2301 were part of the group treated with dronedarone hydrochloride.

At randomization, 737 patients with coronary heart disease were part of the placebo group and 668 patients with coronary heart disease were part of the group treated with dronedarone hydrochloride.

321 events were reported in the placebo group versus 233 in the group treated with dronedarone hydrochloride.

Calculated relative risk was equal to 0.740, i.e. a decrease of cardiovascular hospitalization of 26% for patients with coronary heart disease (P=0.0005).

III.27. Results Relating to the Prevention of Death for Patients with Coronary Heart Disease From the 4628 patients included in the trial, 2301 were part of the group treated with dronedarone hydrochloride.

At randomization, 737 patients with coronary heart disease were part of the placebo group and 668 patients with coronary heart disease were part of the group treated with dronedarone hydrochloride.

66 events were reported in the placebo group versus 39 in the group treated with dronedarone hydrochloride.

Calculated relative risk was equal to 0.643, i.e. a decrease of death of 36% for patients with coronary heart disease (P=0.0273).

III.28. Results Relating to the Prevention of Cardiovascular Death for Patients with Coronary Heart Disease From the 4628 patients included in the trial, 2301 were part of the group treated with dronedarone hydrochloride.

At randomization, 737 patients with coronary heart disease were part of the placebo group and 668 patients with coronary heart disease were part of the group treated with dronedarone hydrochloride.

47 events were reported in the placebo group versus 26 in the group treated with dronedarone hydrochloride.

Calculated relative risk was equal to 0.602, i.e. a decrease of cardiovascular death of 40% (P=0.0355).

III.29. Results Relating to the Prevention of Cardiovascular Hospitalization and Death in Patients with Cardiovascular Risk Factors

|  | N | HR (95% CI) |
|---|---|---|
| Age ≧ 75 years | 1925 | 0.75 (0.65, 0.87) |
| Hypertension | 3995 | 0.77 (0.69, 0.85) |
| Diabetes | 945 | 0.75 (0.61, 0.91) |
| Prior cerebrovascular accident or systemic embolism | 616 | 0.80 (0.62, 1.02) |
| Left atrium diameter >= 50 mm | 955 | 0.77 (0.63, 0.94) |
| LVEF < 0.40 | 338 | 0.72 (0.51, 1.00) |

Consequently, these results show a decrease of respectively 25%, 23%, 25%, 20%, 23%, 28% of cardiovascular hospitalization and death in patients with at least one of each above cardiovascular risk factors.

III.30. Results Relating to the Prevention of Cardiovascular Hospitalization

|  | Placebo (N = 2327) | Dronedarone (N = 2301) | HR (95% CI) |
|---|---|---|---|
| Any cardiovascular hospitalization | 859 (36.9%) | 675 (29.3%) | 0.745 [0.673-0.824] |
| Atherosclerosis related (if not otherwise specified) | 8 (0.3%) | 11 (0.5%) | 1.282 [0.516-3.187] |
| Myocardial infarction or unstable angina | 61 (2.6%) | 48 (2.1%) | 0.742 [0.508-1.083] |
| Stable angina pectoris or atypical chest pain | 41 (1.8%) | 45 (2.0%) | 1.042 [0.682-1.591] |
| Syncope | 24 (1.0%) | 21 (0.9%) | 0.836 [0.465-1.501] |
| TIA or stroke (except intracranial hemorrhage) | 35 (1.5%) | 28 (1.2%) | 0.751 [0.457-1.235] |
| Atrial fibrillation and other supraventricular rhythm disorders | 457 (19.6%) | 296 (12.9%) | 0.616 [0.532-0.713] |
| Non-fatal cardiac arrest | 2 (<0.1%) | 3 (0.1%) | 1.442 [0.241-8.632] |
| Cardiovascular surgery except cardiac transplantation | 23 (1.0%) | 21 (0.9%) | 0.852 [0.472-1.540] |
| Implantation of a pacemaker, ICD or any other cardiac device | 29 (1.2%) | 32 (1.4%) | 1.041 [0.630-1.721] |
| Transcutaneous coronary, cerebrovascular or peripheral procedure | 31 (1.3%) | 27 (1.2%) | 0.817 [0.488-1.369] |

|  | Placebo (N = 2327) | Dronedarone (N = 2301) | HR (95% CI) |
|---|---|---|---|
| Blood pressure related (hypotension, hypertension; except syncope) | 21 (0.9%) | 21 (0.9%) | 0.949 [0.518-1.738] |
| Cardiovascular infection | 0 (0%) | 4 (0.2%) | NA |
| Major bleeding (requiring two or more units of blood or any intracranial hemorrhage) | 24 (1.0%) | 21 (0.9%) | 0.816 [0.454-1.466] |
| Pulmonary embolism or deep vein thrombosis | 3 (0.1%) | 10 (0.4%) | 3.159 [0.869-11.478] |
| Worsening heart failure, including pulmonary edema or dyspnea of cardiac origin | 92 (4.0%) | 78 (3.4%) | 0.805 [0.595-1.089] |
| Ventricular extrasystoles | 1 (<0.1%) | 1 (<0.1%) | 0.973 [0.061-15.560] |
| Ventricular tachycardia (non-sustained and sustained) | 6 (0.3%) | 6 (0.3%) | 0.952 [0.307-2.951] |
| Ventricular fibrillation | 1 (<0.1%) | 1 (<0.1%) | 0.943 [0.059-15.083] |
| Other ventricular arrhythmia | 0 (0%) | 1 (<0.1%) | NA |

III.31. Results Relating to the Prevention of Cardiovascular Hospitalization not Due to a Supraventricular Arrhythmia Such as Atrial Fibrillation or Flutter AFL hospitalizations on dronedarone was mainly due to fewer hospitalizations for worsening heart failure, MI or unstable angina, or stroke or TIA.

|  | Placebo (N = 2327) | Dronedarone (N = 2301) | HR (95% CI) |
|---|---|---|---|
| Any non-AF cardiovascular hospitalization | 511 (22.0%) | 438 (19.0%) | 0.855 [0.753-0.972] |
| Atherosclerosis related (if not otherwise specified) | 10 (0.4%) | 11 (0.5%) | 1.094 [0.464-2.575] |
| Myocardial infarction or unstable angina | 71 (3.1%) | 52 (2.3%) | 0.730 [0.511-1.045] |
| Stable angina pectoris or atypical chest pain | 53 (2.3%) | 51 (2.2%) | 0.962 [0.655-1.412] |
| Syncope | 28 (1.2%) | 23 (1.0%) | 0.822 [0.474-1.427] |
| TIA or stroke (except intracranial hemorrhage) | 43 (1.8%) | 32 (1.4%) | 0.742 [0.469-1.172] |
| Non-fatal cardiac arrest | 2 (<0.1) | 3 (0.1%) | 1.504 [0.251-9.000] |
| Cardiovascular surgery except cardiac transplantation | 28 (1.2%) | 24 (1.0%) | 0.853 [0.495-1.472] |
| Implantation of a pacemaker, ICD or any other cardiac device | 56 (2.4%) | 46 (2.0%) | 0.819 [0.555-1.210] |
| Transcutaneous coronary, cerebrovascular or peripheral procedure | 40 (1.7%) | 31 (1.3%) | 0.773 [0.484-1.235] |
| Blood pressure (hypotension, hypertension, not syncope) | 26 (1.1%) | 25 (1.1%) | 0.960 [0.554-1.662] |
| Cardiovascular infection | 0 (0%) | 4 (0.2%) | NA |
| Major bleeding (requiring two or more units of blood or any intracranial hemorrhage) | 28 (1.2%) | 27 (1.2%) | 0.960 [0.566-1.628] |
| Pulmonary embolism or deep vein thrombosis | 4 (0.2%) | 11 (0.5%) | 2.713 [0.864-8.521] |
| Worsening heart failure, including pulmonary edema or dyspnea of cardiac origin | 113 (4.9%) | 89 (3.9%) | 0.787 [0.596-1.039] |
| Ventricular extrasystoles | 1 (<0.1) | 1 (<0.1) | 1.005 [0.063-16.062] |
| Ventricular tachycardia (non-sustained and sustained) | 7 (0.3%) | 6 (0.3%) | 0.857 [0.288-2.550] |
| Ventricular fibrillation | 1 (<0.1) | 1 (<0.1) | 0.997 [0.062-15.940] |
| Other ventricular arrhythmia | 0 (0%) | 1 (<0.1) | NA |

For example, dronedarone was associated with a 14.5% reduction in the risk of a first cardiovascular hospitalization not due to a supraventricular arrhythmia (HR [95% CI] 0.855 [0.753-0.972]). As noted below, the lower number of non-AF/

What is claimed is:

1. A method of decreasing a risk of cardiovascular hospitalization in a patient, said method comprising administering to said patient an effective amount of dronedarone or a pharmaceutically acceptable salt thereof, twice a day with a morning and an evening meal, wherein said patient does not have severe heart failure, (i) wherein severe heart failure is indicated by: a) NYHA Class IV heart failure or b) hospitalization for heart failure within the last month; and (ii) wherein said patient has a history of, or current, paroxysmal or persistent non-permanent atrial fibrillation or flutter; and (iii) wherein the patient has at least one cardiovascular risk factor selected from the group consisting of:
   i. an age greater than or equal to 75;
   ii. hypertension;
   iii. diabetes;
   iv. a history of cerebral stroke or of systemic embolism;
   v. a left atrial diameter greater than or equal to 50 mm; and
   vi. a left ventricular ejection fraction less than 40%.

2. The method according to claim 1, wherein said cardiovascular hospitalization is hospitalization for atrial fibrillation.

3. The method according to claim 1, wherein the administration of dronedarone or pharmaceutically acceptable salt thereof prevents cardiovascular hospitalization.

4. The method according to claim 1, wherein said patient further receives a diuretic-based treatment.

5. The method according to claim 4, wherein said diuretic is a non-potassium-sparing diuretic.

6. The method according to claim 1, wherein the dose of dronedarone administered per day, orally, is less than or equal 800 mg, measured in base form.

7. A method of treating a patient with a recent history of or current atrial fibrillation or flutter, said method comprising administrating to said patient a therapeutically effective amount of dronedarone, or a pharmaceutically acceptable salt thereof, twice a day with a morning and an evening meal, wherein said patient does not have severe heart failure, (i) wherein severe heart failure is indicated by: a) NYHA Class IV heart failure or b) hospitalization for heart failure within the last month, and (ii) wherein said atrial fibrillation or flutter is non-permanent and is paroxysmal or persistent; and (iii) wherein the patient has at least one cardiovascular risk factor selected from the group consisting of:
   i. an age greater than or equal to 75;
   ii. hypertension;
   iii. diabetes;
   iv. a history of cerebral stroke or of systemic embolism;
   v. a left atrial diameter greater than or equal to 50 mm; and
   vi. a left ventricular ejection fraction less than 40%.

8. A method of decreasing a risk of hospitalization for atrial fibrillation in a patient having a history of atrial fibrillation or atrial flutter, said method comprising administering dronedarone, or a pharmaceutically acceptable salt thereof, twice a day with a morning and an evening meal to a patient in need thereof, wherein said patient does not have severe heart failure, (i) wherein severe heart failure is indicated by: a) NYHA Class IV heart failure or b) hospitalization for heart failure within the last month, and (ii) wherein said atrial fibrillation or flutter is non-permanent and is paroxysmal or persistent; and (iii) wherein the patient has at least one cardiovascular risk factor selected from the group consisting of:
   i. an age greater than or equal to 75;
   ii. hypertension;
   iii. diabetes;
   iv. a history of cerebral stroke or of systemic embolism;
   v. a left atrial diameter greater than or equal to 50 mm; and
   vi. a left ventricular ejection fraction less than 40%.

9. The method according to claim 1, wherein the severe heart failure is indicated by NYHA Class IV heart failure.

10. The method of claim 1, wherein the administration of said effective amount is maintained for at least 12 months.

11. The method of claim 1, wherein the administration of said effective amount of dronedarone or a pharmaceutically acceptable salt thereof is maintained to decrease the risk of cardiovascular hospitalization.

12. The method according to claim 1, wherein said patient has a history of paroxysmal or persistent atrial fibrillation or atrial flutter.

13. The method of claim 8, wherein the dose of dronedarone administered per day, orally, is less than or equal 800 mg, measured in base form.

14. The method claim 1, wherein the severe heart failure is indicated by hospitalization for heart failure within the last month.

15. The method of claim 7, wherein the severe heart failure is indicated by NYHA Class IV heart failure.

16. The method of claim 8, wherein the severe heart failure is indicated by NYHA Class IV heart failure.

17. The method of claim 7, wherein the severe heart failure is indicated by hospitalization for heart failure within the last month.

18. The method of claim 8, wherein the severe heart failure is indicated by hospitalization for heart failure within the last month.

19. The method according to claim 1, wherein the risk factor is an age greater than or equal to 75.

20. The method according to claim 7, wherein the risk factor is an age greater than or equal to 75.

21. The method according to claim 8, wherein the risk factor is an age greater than or equal to 75.

22. The method according to claim 1, wherein the risk factor is hypertension.

23. The method according to claim 7, wherein the risk factor is hypertension.

24. The method according to claim 8, wherein the risk factor is hypertension.

* * * * *